(12) United States Patent
Sylvester

(10) Patent No.: US 9,241,972 B2
(45) Date of Patent: Jan. 26, 2016

(54) USE OF WNT AGENTS TO PREVENT HYPOXIC INJURY

(75) Inventor: Karl G. Sylvester, Los Altos, CA (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 12 days.

(21) Appl. No.: 14/007,309

(22) PCT Filed: Mar. 27, 2012

(86) PCT No.: PCT/US2012/030665
§ 371 (c)(1),
(2), (4) Date: Dec. 30, 2013

(87) PCT Pub. No.: WO2012/135176
PCT Pub. Date: Oct. 4, 2012

(65) Prior Publication Data
US 2014/0141061 A1    May 22, 2014

Related U.S. Application Data

(60) Provisional application No. 61/468,356, filed on Mar. 28, 2011.

(51) Int. Cl.
*A61K 38/18*   (2006.01)
*A61K 38/17*   (2006.01)
*A61L 27/54*   (2006.01)

(52) U.S. Cl.
CPC ................ *A61K 38/17* (2013.01); *A61K 38/18* (2013.01); *A61L 27/54* (2013.01); *A61L 2300/252* (2013.01); *A61L 2300/626* (2013.01)

(58) Field of Classification Search
CPC ............. A61K 38/18; A61L 2300/252; A61L 2300/626
See application file for complete search history.

(56) References Cited

U.S. PATENT DOCUMENTS

| 7,764,995 | B2 | 7/2010 | Girouard et al. | |
| 2003/0114382 | A1* | 6/2003 | Walsh | 514/12 |
| 2004/0213766 | A1 | 10/2004 | Francois | |
| 2005/0043260 | A1 | 2/2005 | Schneider et al. | |
| 2005/0261189 | A1* | 11/2005 | Larsen et al. | 514/12 |
| 2006/0115460 | A1* | 6/2006 | Naughton | 424/93.21 |
| 2009/0047276 | A1* | 2/2009 | Moon et al. | 424/130.1 |
| 2010/0199362 | A1 | 8/2010 | McMahon et al. | |
| 2011/0033434 | A1* | 2/2011 | Ratcliffe et al. | 424/93.71 |
| 2013/0309211 | A1* | 11/2013 | Deb | 424/93.21 |

FOREIGN PATENT DOCUMENTS

WO    WO2007001351 A1    1/2007

OTHER PUBLICATIONS

Gherghe et al., FASEB J. Jun. 2011;25(6):1836-43 Published online Feb. 14, 2011, doi: 10.1096/fj.10-172981 fj.10-172981.*
Hoogeboom et al., "Should I stay or should I go: beta-catenin decides under stress", Biochim Biophys Acta (2009), 1796(2):63-74.
Kaidi et al., "Interaction between beta-catenin and HIF-1 promotes cellular adaptation to hypoxia", nat Cell Biol (2007), 9(2):210-217.
Lim et al., "Hypoxia-Inducible Factor-1A Obstructs a Wnt Signaling Pathway by Inhibiting the hARD1-Mediated Activation of B-Catenin", Cancer Res (2008), 68(13):5177-5184.

* cited by examiner

*Primary Examiner* — Daniel C Gamett
(74) *Attorney, Agent, or Firm* — Bozicevic, Field & Francis LLP; Pamela J. Sherwood

(57) ABSTRACT

Methods and compositions are provided for the therapeutic use of Wnt proteins or Wnt agonists in protecting tissue from the adverse effects of hypoxia.

12 Claims, 15 Drawing Sheets

Favorable Conditions

Unfavorable Conditions
(Ischemia and Reperfusion Injury)

USE OF WNT AGENTS TO PREVENT HYPOXIC INJURY

CROSS REFERENCE TO RELATED APPLICATIONS

Pursuant to 35 U.S.C. §119(e), this application claims priority to the filing date of the U.S. Provisional Patent Application Ser. No. 61/468,356 filed Mar. 28, 2011; the complete disclosure of which is herein incorporated by reference.

BACKGROUND OF THE INVENTION

Two related physiological conditions are ischemia and hypoxia. Ischemia refers to an inadequate flow of blood to a part of the body, caused by constriction or blockage of the blood vessels supplying it, and hypoxia is a shortage of oxygen, which may be the result of an ischemic condition, or may be the result of environmental and other causes.

There are a number of conditions in which ischemia is a factor. Ischemia is a feature of heart diseases, transient ischemic attacks, cerebrovascular accidents, ruptured sensitive to inadequate blood supply. Ischemia in brain tissue, for example due to stroke or head injury, causes a process called the ischemic cascade to be unleashed, in which proteolytic enzymes, reactive oxygen species, and other harmful chemicals damage and may ultimately kill brain tissue. Insufficient blood supply causes tissue to become hypoxic. In very aerobic tissues such as heart and brain, at body temperature necrosis due to ischemia usually takes about 3-4 minutes before becoming irreversible.

Restoration of blood flow after a period of ischemia can actually be more damaging than the ischemia. Reintroduction of oxygen causes a greater production of damaging free radicals as well as allowing, via removal of the extracellular acidotic conditions, influx of calcium and thus calcium overloading. The absence of oxygen and nutrients from blood creates a condition in which the restoration of circulation results in inflammation and oxidative damage through the induction of oxidative stress rather than restoration of normal function. Overall this results in reperfusion injury which can result in potentially fatal cardiac arrhythmias, also necrosis can be greatly accelerated.

The damage of reperfusion injury is due in part to the inflammatory response of damaged tissues. White blood cells, carried to the area by the newly returning blood, release a host of inflammatory factors such as interleukins as well as free radicals in response to tissue damage. The restored blood flow reintroduces oxygen within cells that damages cellular proteins, DNA, and the plasma membrane. Damage to the cell's membrane may in turn cause the release of more free radicals. Such reactive species may also act indirectly in redox signaling to turn on apoptosis. Leukocytes may also build up in small capillaries, obstructing them and leading to more ischemia.

Reperfusion injury plays a part in the brain's ischemic cascade, which is involved in stroke and brain trauma. Similar failure processes are involved in brain failure following reversal of cardiac arrest. Reperfusion injury is also associated with graft transplantation.

A common feature of tissue hypoxia is increased cellular reactive oxygen species (ROS), macromolecular damage and permanent cellular injury. For example, hypoxic liver injury from a variety of etiologies including liver congestion, toxins, bile acids, cancer and ischemia-reperfusion after liver resection or transplantation is in part mediated by oxidative stress. The liver requires a constant supply of oxygen to maintain adequate energy production for hepatocyte homeostasis and survival. Therefore, hepatocytes have evolved a number of protective mechanisms in order to mitigate oxidative injury. The net result of overwhelming injury when this process fails is hepatocyte death and liver fibrosis leading to progressive disease.

Compositions and methods that alleviate the adverse effects of hypoxia and ischemia, in particular injury resulting from ischemia reperfusion, are of great interest for clinical and other uses. The present invention addresses this issue.

PUBLICATIONS

WO/20070001351. METHODS FOR TREATING ISCHEMIC TISSUE; US20100199362. WNT LIGANDS INVOLVED IN BLOOD-BRAIN BARRIER DEVELOPMENT AND USES THEREFOR; U.S. Pat. No. 7,764,995. Method and apparatus to modulate cellular regeneration post myocardial infarct; US20050043260, Wnt as a factor for cardiac myogenesis.

SUMMARY OF THE INVENTION

Methods and compositions are provided for the therapeutic use of Wnt proteins or Wnt agonists, which may be referred to herein as Wnt agents, in protecting tissue from the adverse effects of hypoxia. In some methods of the invention, the Wnt agents are administered to a tissue at risk of hypoxic damage relating to reperfusion injury, including without limitation the treatment of tissues for transplantation in vivo and ex vivo prior to, during, and/or after transplantation. For example, an organ stored for transplantation may be contacted with an effective dose of a Wnt agent to reduce the adverse effects of reperfusion upon transplantation. In some methods of the invention the tissue is one or more of heart tissue, kidney tissue, skin tissue, liver tissue, and lung tissue. The methods of the invention also find use in the treatment of tissue at risk of reperfusion injury outside of transplantation settings, for example as associated with stroke, crush injuries, cardiac ischemia, etc., where an effective dose of a Wnt agent is administered to the individual at risk of reperfusion injury.

Oxygen radicals that are common causes of tissue damage relating to ischemia and reperfusion. It is demonstrated herein that Wnt signal transduction through β-catenin is impacted by cellular redox balance, and specifically hypoxia-induced oxidative stress. In response to changes in redox balance, β-catenin is post-translationally altered to have increased binding to HIF-1, mitigating tissue damage that results from free radicals.

In certain embodiments, the subject is undergoing treatment for a cardiac condition, thus the condition increases the subject's risk for ischemia, developing a stroke, or hemorrhage. The treatment, for example, may comprise the use of thrombolytic agents to treat myocardial infarctions. Still further, the subject may be at risk of ischemia or developing a stroke because the subject suffers from atrial fibrillation or a clotting disorder, for example. Other subjects that are at risk for ischemia or developing a stroke include subjects that are at risk of developing pulmonary emboli, subjects undergoing surgery (e.g., vascular surgery or neurological surgery), or subjects undergoing treatments that increase their risk for developing a stroke, for example, the treatment may comprise cerebral/endovascular treatment, angiography or stent placement. In other embodiments, the subject may be undergoing treatment for vascular disease that could place the spinal cord at risk for ischemia, such as surgery requiring aortic cross-clamping, surgery for abdominal aortic aneurysm, etc. In other embodiments, the patient may be undergoing surgery for a spinal or spinal cord condition, including discectomy, fusion, laminectomy, extradural or intradural surgery for tumor or mass etc., that would place the spinal cord at risk of injury. In some embodiments of the invention, the subject has a chronic condition, whereas in other embodiments of the invention, the subject does not have a chronic condition, such as a short-term condition.

The Wnt agent may be delivered directly to the site of the affected tissue, or may be delivered ex vivo to the tissue of interest. In transplantation, the Wnt agent may be provided immediately before, during or after the tissue is introduced, and in some embodiments is delivered within 1, 2, 3, 4, 5, 6, 7 days following transplantation. In other incidents of reperfusion injury the Wnt agent may be provided prior to or immediately after reperfusion. The Wnt agent may be transiently provided over a short, defined period of time, for example as a single bolus, as a continuous injection for a short period of time, e.g. not more than about 48 hours, not more than about 24 hours, not more than about 12 hours, etc., as repeated bolus doses for a short period of time, e.g. not more than about 48 hours, not more than about 24 hours, not more than about 12 hours, etc., and the like.

In some embodiments of the invention, a pharmaceutical composition for in vivo or ex vivo administration comprises a therapeutically effective dose of a Wnt protein, where the Wnt protein is inserted in the non-aqueous phase of a lipid structure, e.g. in the surface of a liposome, micelle, lipid raft, etc., in an emulsion, and the like. In some embodiments the Wnt protein is presented in its active conformation on an outer liposome membrane or micelle. Where the lipid structure is a liposome it is desirable that the Wnt protein not be encapsulated within the liposome, e.g. in an aqueous phase. The lipid-containing particles typically display copies of a wnt polypeptide, the particles comprising at least one copy of a wnt polypeptide bearing at least one lipid moiety, where the composition contains at least 50% of the Wnt polypeptides displayed on the exterior surface of the particle. In some embodiments of the invention, the Wnt agent is a mammalian protein, including, without limitation, human Wnt proteins. In other embodiments of the invention the Wnt agent is an agonist of frizzled, e.g. antibodies, peptides, small molecules, etc.

The invention also relates to assays designed to screen for compounds or compositions that modulate β-catenin activity, including acetylation/deacetylation of β-catenin by Sirt1, particularly compounds or compositions that act as wnt agonists and that increase β-catenin binding to HIF-1, and thereby prevents and/or treats an ischemic episode. To this end, cell-based assays or non-cell based assays can be used to detect compounds that interact with, e.g., bind to, β-catenin or a component of the b-catenin signaling pathway. Candidate compounds may be further assessed in an assay designed to detect β-catenin binding to HIF-1 in response to altered cellular redox conditions.

In particular aspects, there is a kit of the invention that comprises one or more of a Wnt agent in a pharmaceutically acceptable formulation, an organ transplantation therapeutic compound, or an organ transplantation apparatus. In another embodiment, there is a kit comprising two or more of the following, each of which is housed in a suitable container: a Wnt polypeptide or Wnt agonist; an organ transplant therapeutic compound; and an organ transplant apparatus. The organ transplant therapeutic compound may be selected from the group consisting of an immunosuppressant, an antiviral compound, an antibacterial compound, an antifungal compound, an antacid, or a combination or mixture thereof, in particular embodiments. In specific aspects, the organ transplantation apparatus comprises one or more of a scalpel, a needle, a thread, a suture, or a staple.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

Figure 2A:
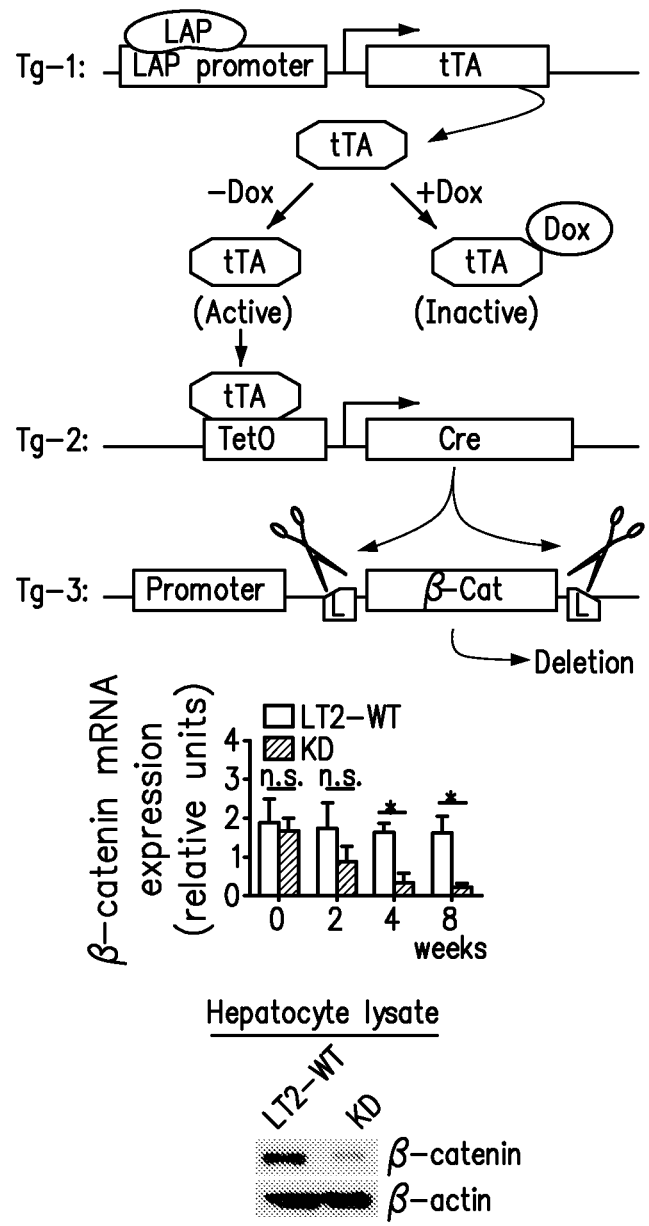
FIG. 2. β-catenin knockdown mice are more susceptible to hepatic I/R injury.
  (A) Schematic strategy for the generation of LT2-KD mouse. qRT-PCR demonstrates a significant reduction of β-catenin mRNA in LT2-KD livers after 4 weeks of dox-withdrawal. Immunoblot shows a remarkable knockdown at its protein level in LT2-KD hepatocytes.
  (B) Hepatocellular injury, as evidenced by elevated serum transaminases, is significantly increased in LT2-KD mice after ischemia and I/R.
  (C) Severe liver damage, increased apoptosis and elevated ROS is detected in LT2-KD mice after ischemia and I/R. Representative liver histology of sham (a,b), ischemia (c-f) or I/R (i-l)-treated livers. Apoptosis is measured by TUNEL staining after ischemia (g,h) or I/R (m,n). Intracellular ROS levels are detected by DHE staining after I/R (o,p).
  (D) LT2-KD livers are more susceptible to I/R-induced apoptosis. Quantification of TUNEL-positive cells/10 HPF in ischemia or I/R-treated livers (see FIG. 2C, panel g-h,m-n). Immunoblot shows more caspase-cleaved K18Asp237 in total liver lysates of LT2-KD mice after I/R.
Figure 2B:
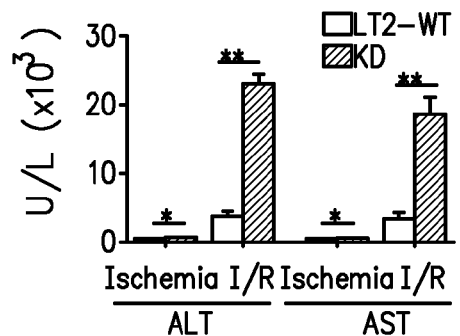
Figure 2D:
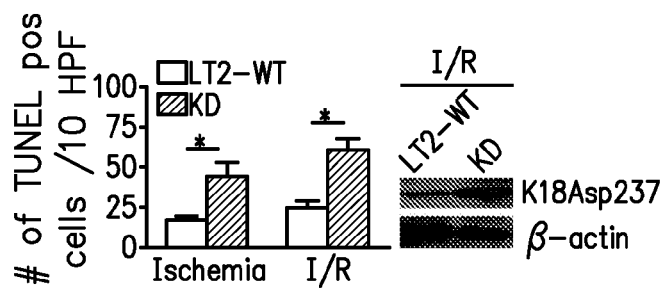
Figure 2E:
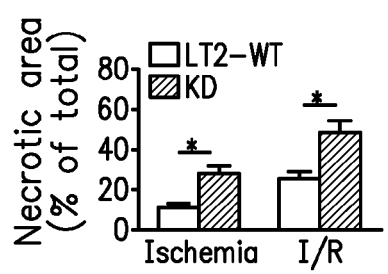
Figure 2F:
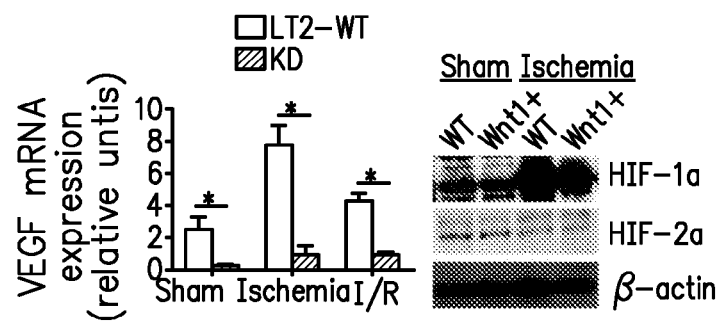
Figure 2C:
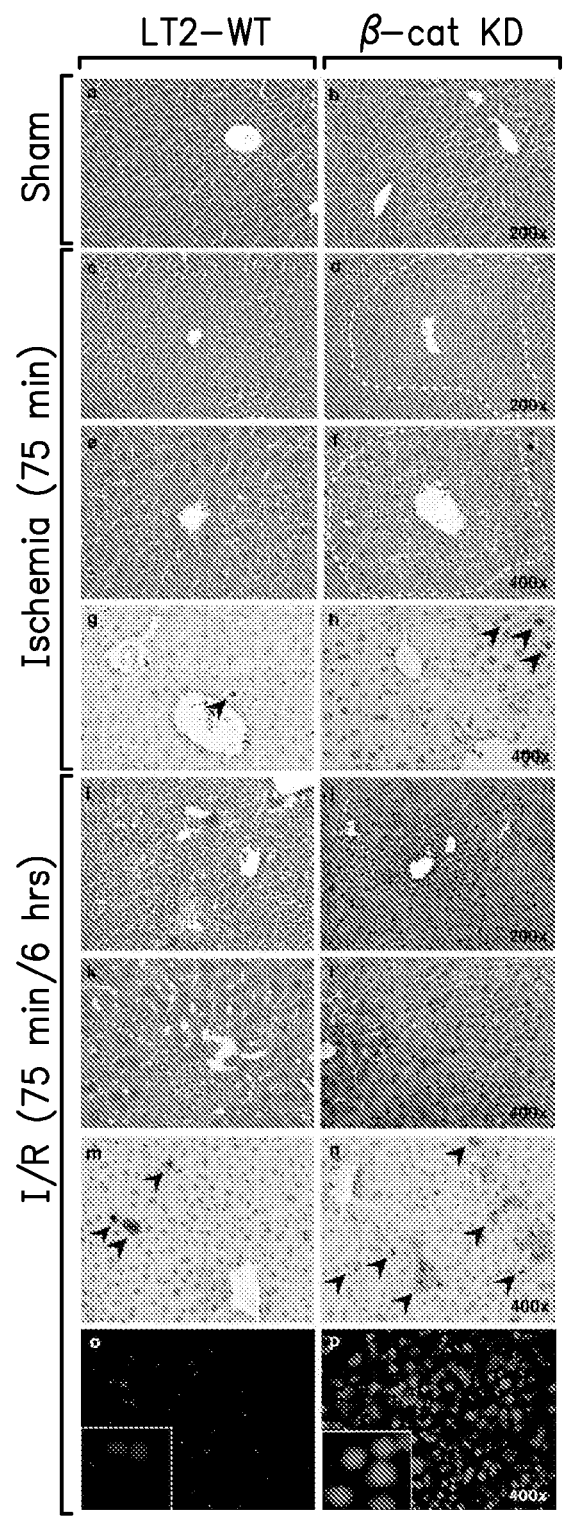

(E) β-catenin deficient livers show increased necrosis by quantification of necrotic areas in ischemia and I/R-treated livers (see FIG. 2C, panel e-f, k-l).

(F) Reduced HIF-1α protein and its target gene (VEGF) mRNA expression in LT2-KD mice. VEGF mRNA expression was measured in sham, ischemia or I/R-treated livers by qRT-PCR. HIF-1α induction after ischemia is significantly impaired in LT2-KD livers as shown by immunoblot (n=5). $*p<0.05$, $**p<0.01$.

FIG. 3. Wnt1 gain-of-function provides strong protection against hepatic I\R Injury.

(A) Bioluminescence imaging of Wnt1+-Luciferase mice show increased liver-specific Luciferase activity upon Dox-withdrawal. Increased Wnt1 and β-catenin target gene (Cyclin D1) protein are expressed in liver lysates of Wnt1+ mice along with a moderate increase in total β-catenin after 3 weeks of dox-removal.

(B) Reduced hepatocellular injury as evidenced by lower transaminases is detected in Wnt1+ mice after ischemia and I/R.

(C) Minor hepatic damage with reduced apoptosis and lower ROS was determined in Wnt1+ livers after ischemia and I/R. Representative liver histology (H&E) of sham (a,b), ischemia (c-f) or I/R (i-l)-treated livers. Apoptosis was measured by TUNEL staining after ischemia (g,h) or I/R (m,n). Intracellular ROS levels were detected by DHE staining after I/R (o,p).

(D) Wnt1+ livers are more resistant to ischemia and I/R-induced apoptosis. Quantification of TUNEL-positive cells/10 HPF in ischemia and I/R-treated livers (see FIG. 3C, panel g-h,m-n). Immunoblot of liver lysates demonstrates diminished levels of caspase-cleaved K18Asp237 in Wnt1+ mice after I/R.

Figure 3A:
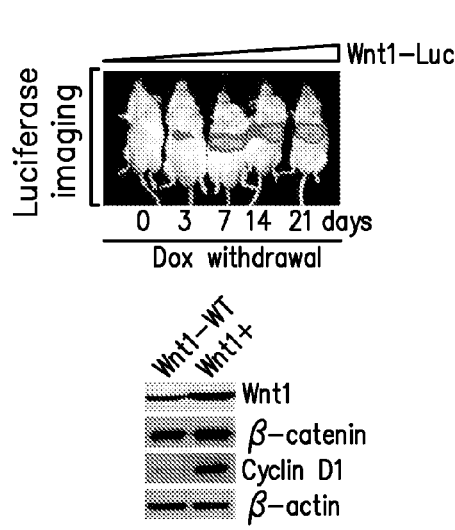
Figure 3B:
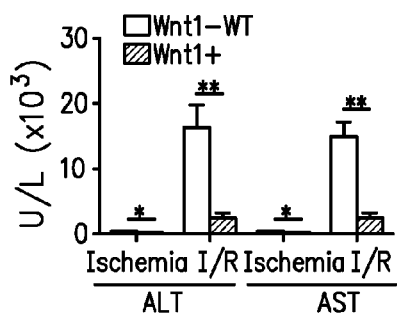
Figure 3C:
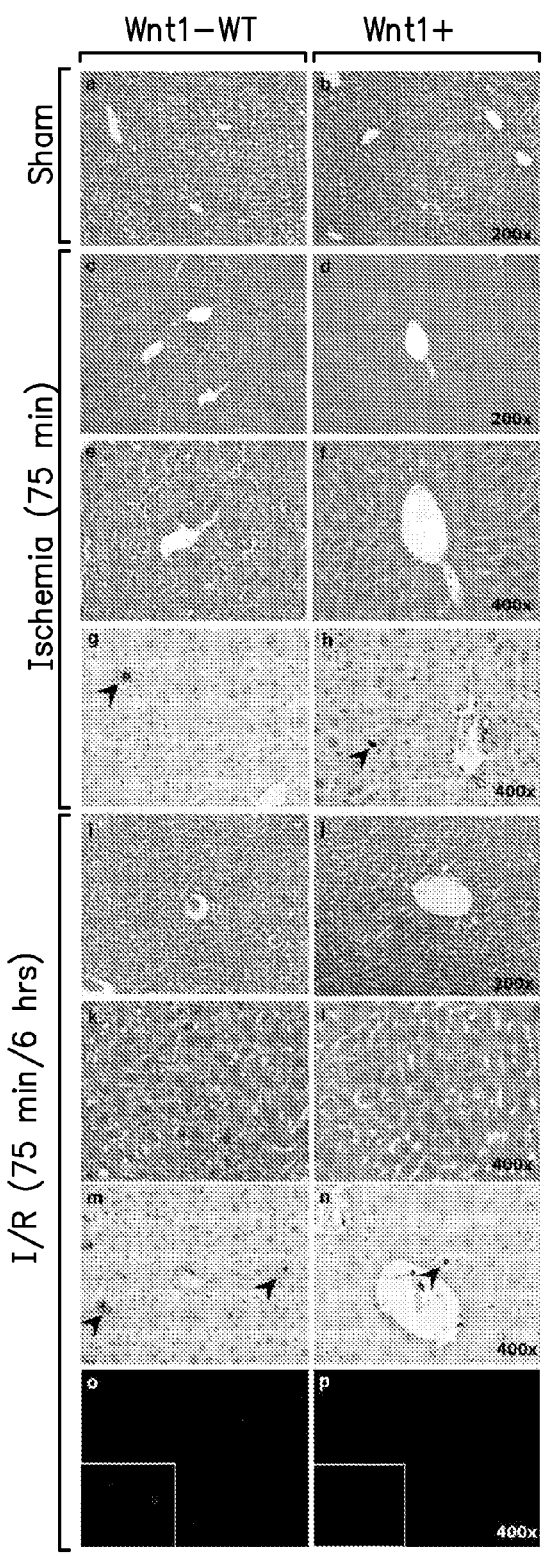
Figure 3D:
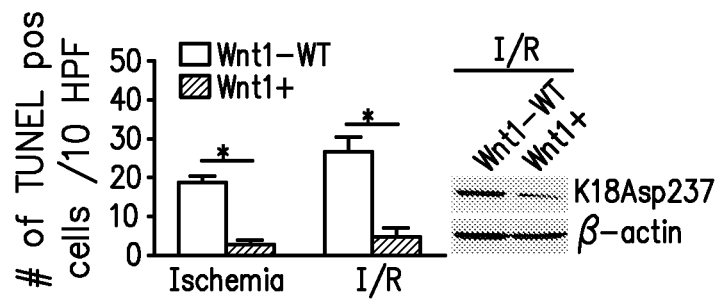
Figure 3E:
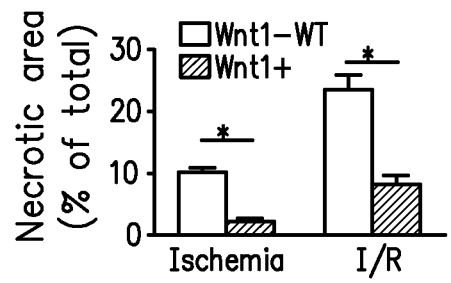
Figure 3F:
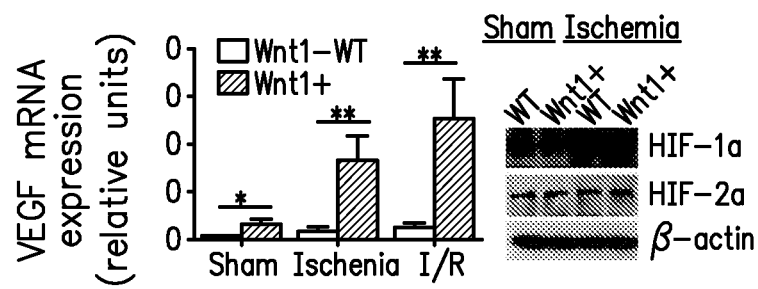

(E) Wn1+ livers show less necrosis in ischemia and I/R-treated livers by quantification of necrotic areas (see FIG. 3C, panel e-f,k-l).

(F) HIF-1α protein and its target gene (VEGF) expression are significantly induced in Wnt1+ livers. VEGF mRNA expression in sham, ischemia and I/R-treated livers was measured by qRT-PCR. HIF-1α but not HIF-2α is significantly augmented in Wnt1+ livers after ischemia as shown by western blot (n=5). $*p<0.05$, $**p<0.01$.

FIG. 4. β-catenin stabilized hepatocytes are resistant to hypoxia-induced apoptosis in vitro by augmented HIF-1α signaling.

(A) S33Y mutant hepatocytes are stress-resistant and proliferate despite hypoxic stress as measured by BrdU ELISA assay.

(B) Under hypoxia, β-catenin mutants show reduced intracellular ROS as determined by DCF-DA flow cytometry.

(C) S33Y hepatocytes are highly resistant to hypoxia or H/R-induced apoptosis as determined by caspase-cleaved K18Asp237. β-catenin mutants show more HIF-1α induction under hypoxia or H/R compared to controls.

(D) Less apoptosis is detected in β-catenin mutants under hypoxia by Caspase-Glo 3/7 activity assay.

(E) TCF reporter activity is decreased in S33Y mutants after hypoxia to a comparable degree as control cells despite a heightened β-catenin/TCF baseline activity.

(F) Augmented HIF-1α reporter activity is detected in β-catenin mutants under hypoxia. RLU=relative light units. $*p<0.05$.

FIG. 5. β-catenin signaling protects hepatocytes against hypoxic injury through augmented HIF-1 signaling.

(A) β-catenin alternatively binds TCF (normoxia) or HIF-1α (hypoxia) depending on oxygen availability. Binding switch was verified by co-immunoprecipitation on HepG2 cell lysates after exposure to normoxia (N) or hypoxia (H) using anti-β-catenin antibody followed by immunoblotting for HIF-1α and TCF4.

(B) Wnt1+ livers show more β-catenin/HIF-1α binding as verified by co-immunoprecipitation in sham or ischemia-treated liver lysates using anti-β-catenin antibody followed by HIF-1α immunoblotting.

(C) Augmented HIF-1α promotor binding in β-catenin mutants after 24 hours hypoxia. For EMSA, 5 µg of nuclear extracts were used for HIF-1/HRE DNA-probe binding reactions.

(D) β-catenin/TCF reporter activity can be reduced by HIF-1α stabilization with $CoCl_2$ (150 µmol/L) under normoxia or hypoxia treatment in AML12 hepatocytes. HIF-1α induction was verified by HRE reporter assay and immunoblot. RLU=relative light units.

(E) HIF-1α inhibition under hypoxia by YC-1 pre-treatment (100 µmmol/L) for 1 hour results in more apoptosis in AML12 hepatocytes as measured by MTT assay and immunoblot for caspase-cleaved K18Asp237. $*p<0.05$.

FIG. 6. Working model explaining β-catenin's role in hepatocyte protection to I/R Injury.

(A) Under normoxic, favorable conditions (upper panel), β-catenin complexes with TCF to promote hepatocyte proliferation.

(B) Under unfavorable conditions like hypoxia or I/R, β-catenin diverts from TCF and preferably associates with HIF-1α to favor cell adaptation and survival (lower, left panel). However, in the absence of β-catenin (lower, middle panel), neither sufficient TCF nor effective HIF-1α signaling can be activated leading to cell death and enhanced liver injury under hypoxic stress. With Wnt/β-catenin signaling gain-of-function (lower, right panel), signaling through both TCF and HIF-1α occurs resulting in increased resistance to I/R and continued proliferation.

Figure 7:
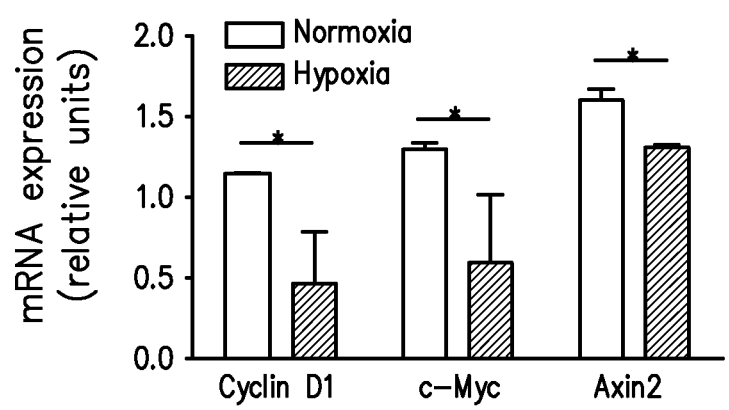
Figure 8A:
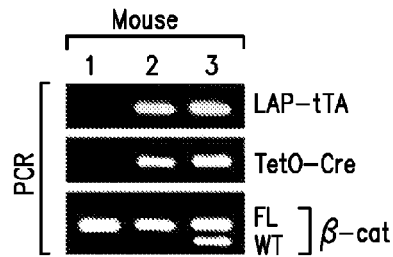
Figure 8B:
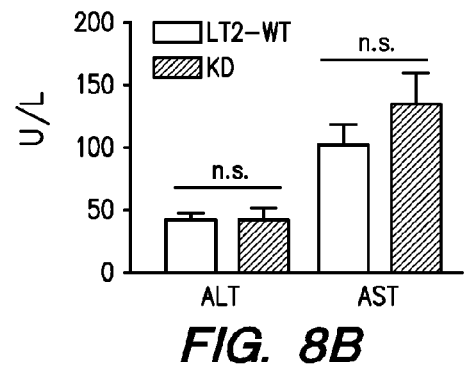
Figure 8C:
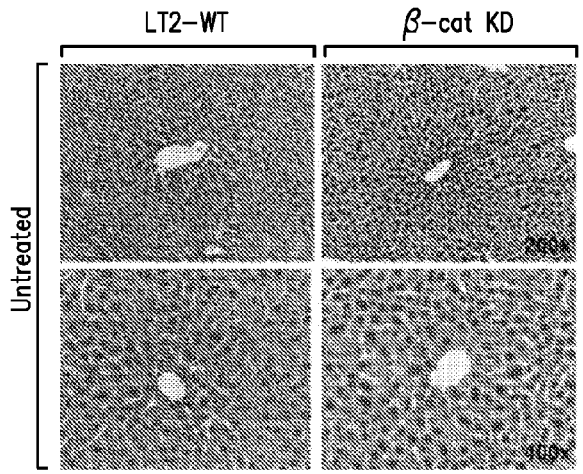
Figure 8D:
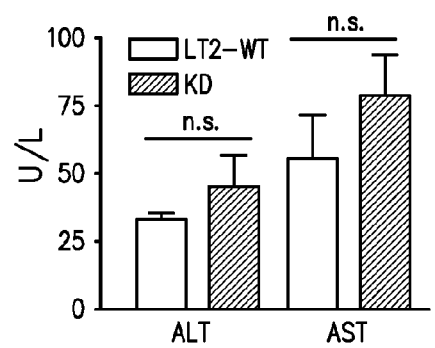
Figure 8E:
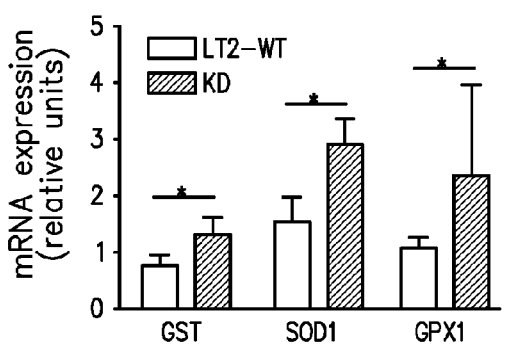
Figure 8F:
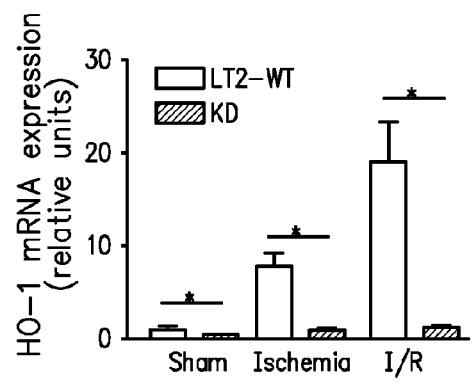

FIG. 7. Significant reduction of β-catenin target genes in response to hypoxia.

(A) Cyclin D1, c-Myc and Axin2 mRNA expression was measured by qRT-PCR in AML12 hepatocytes in response to 1% hypoxia for 24 hours. $*p<0.05$.

FIG. 8. Characterization of β-catenin knockdown mouse.

(A) Genomic DNA was subjected to PCR using indicated primers. Representative PCR demonstrates the relevant alleles for the deletion of β-catenin from hepatocytes after Dox-withdrawal in mouse #2 (KD), but not in #1 (LT2-WT). #3 is used as a heterozygous control for PCR.

(B) No significant difference in liver transaminases, as evidenced by AST and ALT, is detected in untreated LT2-WT and KD mice.

(C) H&E staining of untreated LT2-WT and KD mice shows similar liver histology.

(D) No significant difference in liver transaminases, as evidenced by AST and ALT, is detected between sham-treated LT2-WT and KD mice.

(E) Expression of anti-oxidant genes (GST, SOD1, GPX1) is significantly increased in LT2-KD mice in response to I/R as detected by qRT-PCR.

(F) Impaired induction of HO-1 mRNA expression, a HIF-1α target gene, in sham, ischemia or I/R-treated LT2-KD livers is measured by qRT-PCR (n=5). $*p<0.05$.

Figure 9A:
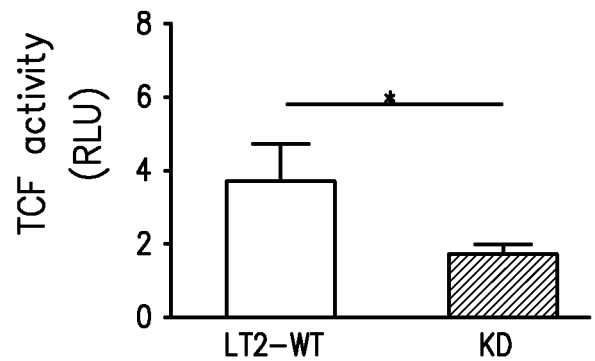
Figure 9B:
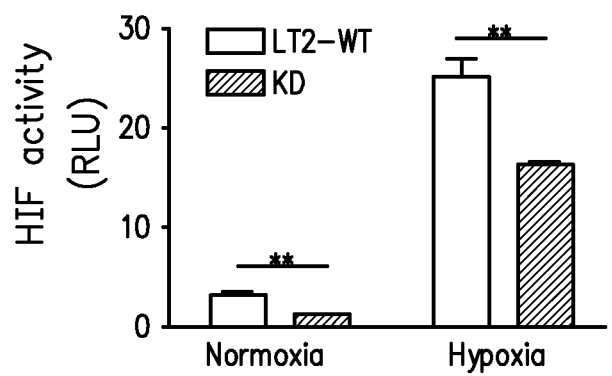
Figure 10A:
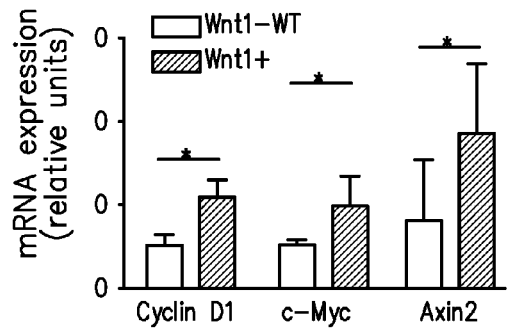
Figure 10B:
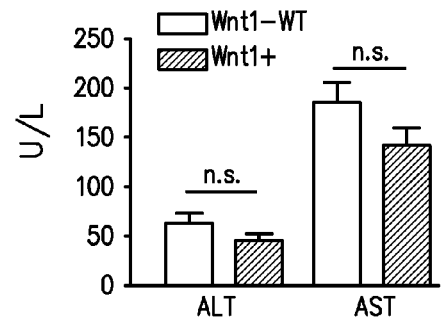
Figure 10C:
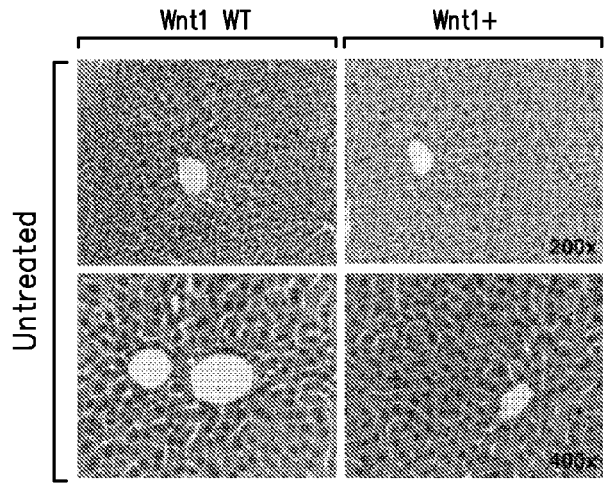
Figure 10D:
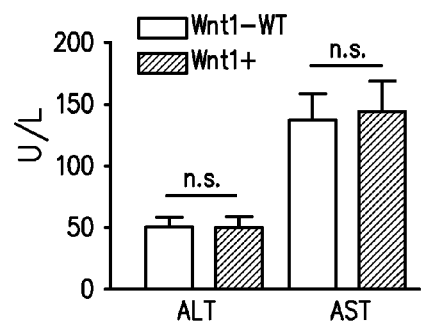
Figure 10E:
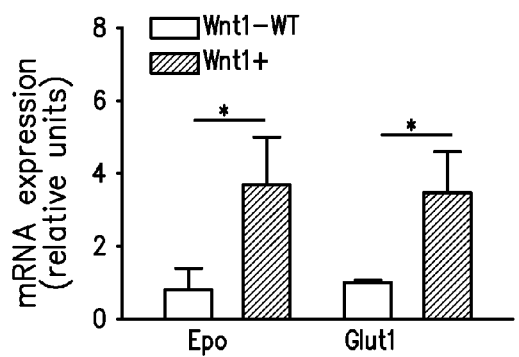
Figure 10F:
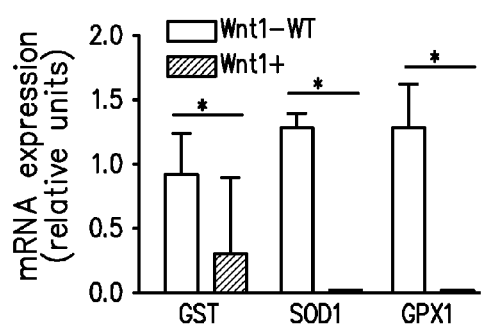

FIG. 9. β-catenin deficient primary hepatocytes lack adaptive signaling through HIF-1β.

(A) Reduced β-catenin/TCF reporter activity was confirmed in isolated β-catenin deficient hepatocytes under hypoxia.

(B) HIF-1 reporter activity is significantly impaired in β-catenin KD primary hepatocytes under either normoxia or hypoxia. RLU=relative light units. *$p<0.05$, **$p<0.01$.

FIG. 10. Characterization of Wnt1+ mouse.
(A) β-catenin target gene (Cyclin D1, c-Myc, Axin2) expression is significantly increased in Wnt1+ mice after 3 weeks of dox-withdrawal as detected by qRT-PCR.
(B) No significant difference in liver transaminases, as evidenced by AST and ALT, was detected in untreated Wnt1-WT and Wnt1+ mice.
(C) H&E staining in untreated Wnt1-WT and Wnt1+ mice shows similar liver histology.
(D) No difference in liver transaminases, as evidenced by AST and ALT, is detected between sham-treated Wnt1-WT and Wnt1+ mice.
(E) HIF-1α target genes (Epo, Glut1) are significantly induced in Wnt1+ livers after I/R as measured by qRT-PCR.
(F) Anti-oxidant genes (GST, SOD1, GPX1) are significantly reduced in Wnt1+ livers after I/R as detected by qRT-PCR (n=5). *$p<0.05$.

Figure 11A:
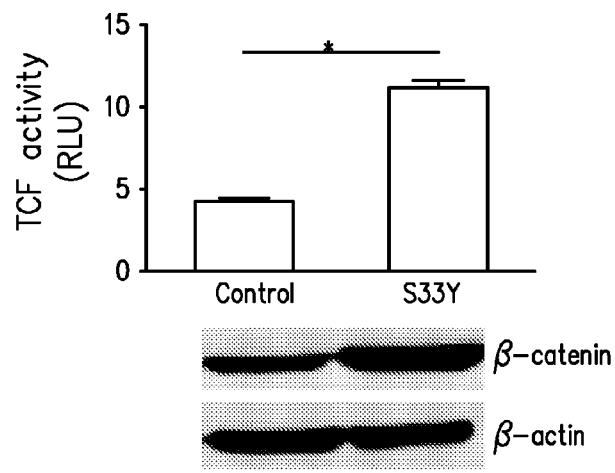
Figure 11B:
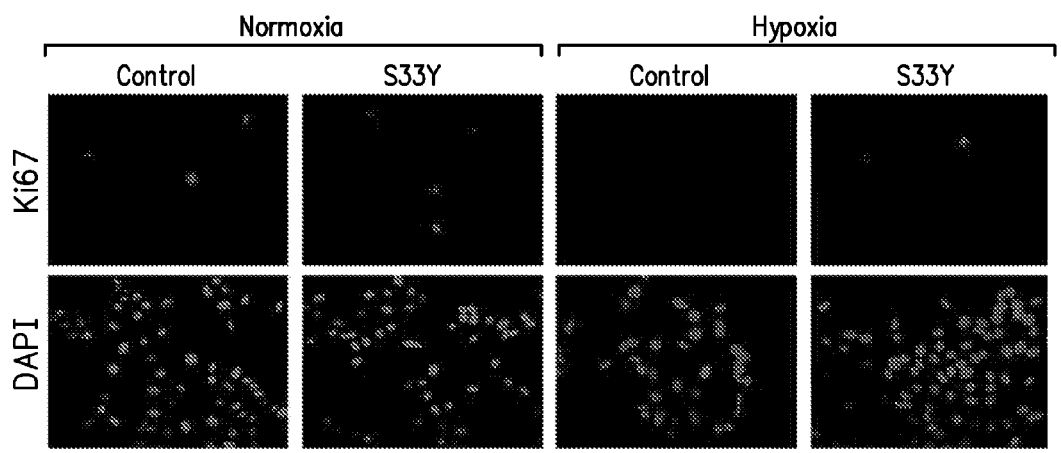
Figure 11C:
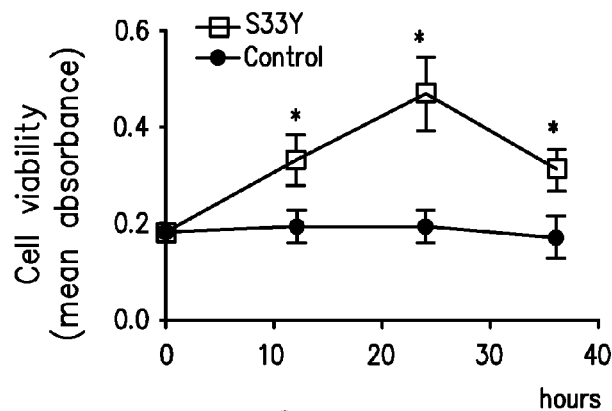

FIG. 11. β-catenin mutants continue proliferation despite hypoxic stress.
(A) TCF reporter activity and β-catenin protein are significantly increased in β-catenin mutants (S33Y) under normoxia. RLU=relative light units.
(B) β-catenin mutants show increased proliferation under normoxia and hypoxia as detected by immunofluorescence staining using Ki-67 antibody (dilution 1:500).
(C) β-catenin mutants are stress resistant and proliferate despite hypoxic stress as measured by MTT assay. *$p<0.05$.

Figure 12:
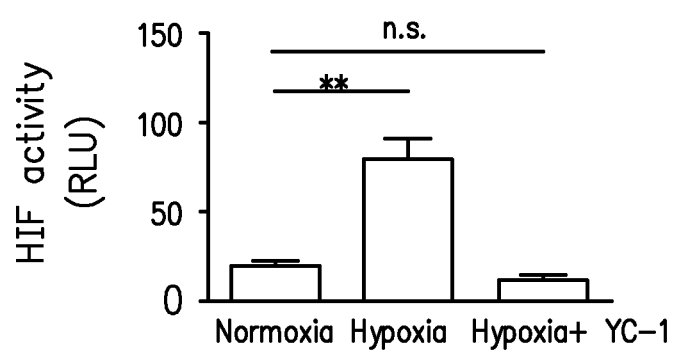

FIG. 12. HIF-1α inhibition results in decreased HIF reporter activity.
(A) Pre-treatment with YC-1 (100 μmol/L) for 1 hour inhibits the hypoxia-induced increase in HIF-1 signal activity in AML12 hepatocytes as measured by reporter assay. RLU=relative light units. **$p<0.01$.

DESCRIPTION OF THE SPECIFIC EMBODIMENTS

Methods and compositions are provided for the therapeutic use of Wnt proteins or Wnt agonists, which may be referred to herein as Wnt agents, in protecting tissue from the adverse effects of hypoxia. In some methods of the invention, the Wnt agents are administered to a tissue at risk of hypoxic damage relating to reperfusion injury, including without limitation the treatment of tissues for transplantation in vivo and ex vivo prior to, during, and/or after transplantation. For example, an organ stored for transplantation may be contacted with an effective dose of a Wnt agent to reduce the adverse effects of reperfusion upon transplantation. In some methods of the invention the tissue is one or more of heart tissue, kidney tissue, skin tissue, liver tissue, and lung tissue. The methods of the invention also find use in the treatment of tissue at risk of reperfusion injury outside of transplantation settings, for example as associated with stroke, crush injuries, cardiac ischemia, etc., where an effective dose of a Wnt agent is administered to the individual at risk of reperfusion injury.

Before the present methods are described, it is to be understood that this invention is not limited to particular methods described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges encompassed within the invention, subject to any specifically excluded limit in the stated range.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a microsphere" includes a plurality of such microspheres and reference to "the stent" includes reference to one or more stents and equivalents thereof known to those skilled in the art, and so forth.

Ischemic episode refers to any circumstance that results in a deficient supply of blood to a tissue, usually due to a restriction in blood supply and/or decreased availability of oxygen to and/or in an organ or tissue of an individual, wherein the restriction may be a constriction and/or an obstruction, for example. The restriction may be due to factors in the blood vessels, in certain cases, and in particular aspects the ischemic episode results in damage or dysfunction of tissue of the organ or tissue and, in some cases, of the function of the organ or tissue itself.

Reperfusion injury refers to tissue damage caused when blood supply returns to the tissue after a period of ischemia. The absence of oxygen and nutrients from blood creates a condition in which the restoration of circulation results in inflammation and oxidative damage through the induction of oxidative stress rather than restoration of normal function It is known that restoration of blood flow following an ischemic episode can be equally if not more damaging than the ischemic episode, because reintroduction of oxygen results in an increased production of damaging free radicals that results in reperfusion injury. Necrosis can be greatly accelerated upon reperfusion, and therefore the compounds of the present invention may be delivered to an individual prior to, upon initiating restoration of blood flow, or during the restoration of blood flow to the body part.

In particular aspects of the invention, an ischemic episode concerns an absolute shortage of blood supply to an organ. In other aspects, the ischemic episode concerns inequity between blood supply (oxygen delivery) and blood demand for sufficient oxygenation of tissue. In certain aspects, an ischemic episode relates to inadequate flow of blood to a part of the body, such as an organ, caused by constriction or blockage of the blood vessels supplying it. For example, angina pectoris (chest pain from insufficient oxygen in the heart) is produced by ischemia of heart muscle. Ischemia may be a characteristic of a variety of maladies, including, for example, heart disease, transient ischemic attacks, cerebrovascular accidents, ruptured arteriovenous malformations, and peripheral artery occlusive disease.

Exemplary organs sensitive to inadequate blood supply include the brain, heart, kidney, lung, liver, eye, intestines, bladder, pancreas, or spleen. Ischemia in brain tissue, for example due to a heart attack, results in an ischemic cascade wherein reactive oxygen species, proteolytic enzymes, and/or other harmful chemicals damage and may ultimately destroy cardiac tissue. Exemplary tissues include, for example, corneal, skin, bone marrow, heart valve, or connective tissue.

In particular embodiments of the invention, an ischemic episode occurs prior to and/or during shock or organ transplantation or is at risk for developing with shock or organ transplantation, and in these exemplary cases the ischemic episode is treated with a compound of the invention.

Coronary artery disease is a major medical problem affecting morbidity and mortality worldwide. Coronary arteries, as well as other blood vessels, can become obstructed, partially or wholly, by for example atherosclerotic plaque. Plaque formation can lead to the impairment of the efficiency of the heart's physiological action and can lead to the inhibition of blood flow to heart, which can lead to heart attack and death. In certain instances, damaged cardiac vasculature (e.g., a narrowed lumen due to atherosclerotic plaque formation) can be treated by techniques such as, for example, balloon angioplasty or percutaneous transluminal coronary angioplasty. In other instances, surgical bypass of the damaged cardiac vessel is necessary.

Coronary artery bypass graft ("CABG") involves performing an anastomosis on a diseased coronary artery to reestablish blood flow to an ischemic portion of the heart. During a typical coronary artery bypass graft procedure using the saphenous vein, a section of the saphenous vein is surgically removed from the leg and the graft is retained ex vivo (out of the body) for a length of time prior to attachment to another blood vessel within the body. In a bypass operation involving such a venous graft, the graft is harvested by a surgically invasive procedure from the leg of the patient and then stored for up to several hours ex vivo (e.g., four hours) as surgery is performed on the heart. Having harvested and stored the saphenous vein or arterial blood vessel conduit and upon completion of the surgery to prepare the heart for grafting, the bypass procedure is performed. The overall short and long term success of the CABG procedure is dependent on several factors including the condition of the graft used, which itself depends on any form of damage during the removal of the graft from the body or deterioration or damage of the graft due to storage conditions. It is therefore of critical importance not only that care be taken in the surgical procedure to remove the blood vessel to be used as the graft in surgical bypass procedures including CABG, but, also that no deterioration or damage occurs in the storage period of the graft prior to attachment to another blood vessel and the resumption of blood flow in that vessel.

In certain embodiments, any vascular graft and any vein/artery (including, for example, saphenous vein, tibial artery (including, for example, posterior tibial artery), mammary artery, radial artery, or any other vein/artery (including, for example, infrainguinal, popliteal, and distal leg arteries)) are included in the invention described herein. Furthermore, the invention is not restricted to nature of the vascular graft with respect to recipient and its origin (i.e., the graft can be either heterologous in nature or autologous in nature). In other certain embodiments, the artery or vein that is to be used for a bypass procedure can be stored in compositions comprising an effective dose of a Wnt agent of the invention prior to the surgical procedure whereby attachment of the bypass graft to the coronary artery (anastomosis) is performed. In further embodiments, compositions comprising an effective dose of a Wnt agent of the invention can be combined with an organ preservation solution or saline for CABG or other transplantation procedure (including, for example, kidney transplant, liver transplant, heart transplant, limb transplant, skin graft, or any other organ transplant).

An organ preservation solution includes, for example, Stanford University solution (see, e.g., Swanson et al., 1988, Journal of Heart Transplantation, 7(6): 456-467); Collins solution; modified Collins solution (see, e.g., Maurer et al., 1990, Transplantation Proceedings, 22(2): 548-550; Swanson et al., supra); University of Wisconsin solution (see, e.g., U.S. Pat. No. 4,798,824, issued to Belzer et al.); modified University of Wisconsin solution (Yeh et al., Ann Thorac Surg. 1990 June; 49(6):932-9); Columbia University solution (see, e.g., U.S. Pat. Nos. 5,552,267 and 5,370,989, and Kayano et al., 1999, J. Thoracic Cardiovascular Surg. 118: 135-144); histidine-tryptophan-ketoglutarate (HTK) solution (see, e.g., Ku et al., Transplantation. 1997 Oct. 15; 64(7):971-5); Celsior (see, e.g., Janssen et al., Transplant International (2003), 16(7): pp. 515-522); isotonic saline solutions, that may contain, in various proportions, salts, sugars, osmotic agents, local anesthetic, buffers, and other such agents (see, e.g., Berdyaev et al., U.S. Pat. No. 5,432,053; Belzer et al.); ViaSpan® (see, e.g., U.S. Pat. Nos. 4,798,824, 4,879,283; and 4,873,230; Taylor, U.S. Pat. No. 5,405,742; Dohi et al., U.S. Pat. No. 5,565,317; Stern et al., U.S. Pat. Nos. 5,370,989 and 5,552,267); solutions comprising pyruvate, inorganic salts supporting cell membrane potential and albumin or fetal calf serum (see, e.g., U.S. Pat. No. 5,066,578); solutions comprising one or more phosphatidic acids or sugars, and lysophosphotidic acids or sugars, together with enhancers such as albumen, optionally delivered in liposomal compositions (see, e.g., U.S. Pat. Nos. 6,495,532 and 6,004,579); other organ preservation solutions (see, e.g., U.S. Pat. No. 7,220,538); or any combination of the foregoing.

The invention also relates to ischemia/hypoxia associated events such as, for example, heart attack, a stroke, tachycardia, atherosclerosis, hypotension (e.g. in septic shock, heart failure), thromboembolism (e.g. pulmonary embolism), outside compression of a blood vessel (e.g. by a tumor), foreign bodies in the circulation (e.g. amniotic fluid in amniotic fluid embolism), sickle cell disease, hemorrhage, or rupture of a vessel (e.g. aortic aneurysm rupture) and organ transplantation and treatments to reduce damage to heart and other organs following heart attack or other ischemic or hypoxic/ischemic events, including reducing damage to, or preserving the integrity and function of an organ in life or following removal of an organ for transplantation. Treatments in these aspects of the invention include administration of a Wnt protein or Wnt agonist, optionally in combination with one or more additional therapeutic compound(s). Organs and tissues that may be treated, preserved, and/or protected by the methods and compositions of the invention include, for example, heart, liver, lung, kidney, blood vessel, gastrointestinal tract organs such as intestine, cornea, and other organs and tissues, including connective tissue such as, for example, ligaments and tendons.

For in vivo administration, the composition(s) of the present invention may be delivered alimentarily or parenterally, for example. Examples of alimentary administration include, but are not limited to orally, buccally, rectally, or sublingually. Parenteral administration can include, but are not limited to intramuscularly, subcutaneously, intraperitoneally, intravenously, intratumorally, intraarterially, intraventricularly, intracavity, intravesical, intrathecal, or intrapleural. The compound can be administered alimentary (e.g., orally, buccally, rectally or sublingually); parenterally (e.g., intravenously, intradermally, intramuscularly, intraarterially, intrathecally, subcutaneously, intraperitoneally, intraventricularly); by intracavity; intravesically; intrapleurally; and/or topically (e.g., transdermally), mucosally, or by direct injection into the brain parenchyma. Other modes of administration may also include topically, mucosally, transdermally, or direct injection into the brain parenchyma, for example.

An effective amount of a Wnt agent that may be administered to an individual or a cell in a tissue or organ thereof includes a dose of about 0.0001 nM to about 2000 µM, for example. More specifically, doses are from about 0.01 nM to about 2000 µM; about 0.01 µM to about 0.05 µM; about 0.05 µM to about 1.0 µM; about 1.0 µM to about 1.5 µM; about 1.5 µM to about 2.0 µM; about 2.0 µM to about 3.0 µM; about 3.0 µM to about 4.0 µM; about 4.0 µM to about 5.0 µM; about 5.0 µM to about 10 µM; about 10 µM to about 50 µM; about 50 µM to about 100 µM; about 100 µM to about 200 µM; about 200 µM to about 300 µM; about 300 µM to about 500 µM; about 500 µM to about 1000 µM; about 1000 µM to about 1500 µM and about 1500 µM to about 2000 µM, for example. Of course, all of these amounts are exemplary, and any amount in-between these points is also expected to be of use in the invention.

In certain embodiments, the invention provides compositions for preserving and/or maintaining a cell, tissue, or organ in vivo, ex vivo and/or in vitro, as well as methods of making and using these compositions. In particular embodiments, the invention is drawn to using the compositions and methods described herein to preserve an organ, limb, cell, or tissue to be transplanted or re-attached. An organ includes, for example, solid organs (e.g., heart, kidney, liver, lung, pancreas, small bowel and other organ of the gastrointestinal tract) and functional parts thereof (e.g., lobes of a liver, kidney, lung, and the like). A cell and tissue includes, for example, cornea, retina, bone, heart valves, tendons, ligaments, cartilage, vasculature, skin, bone marrow, blood cells, stem cells, and other tissues and cells derived from the body.

Such compositions and treatments using these compositions may be administered before an expected or possible ischemic or ischemic/hypoxic incident; may be administered during an ischemic or ischemic/hypoxic incident; and/or may be administered following an ischemic or ischemic/hypoxic incident. For example, an organ removed from a patient for later placement in the patient's body (e.g., a blood vessel used in heart bypass surgery) may be treated before, during, and/or after removal from its place of origin, and may be treated before, during, and/or after its placement in its new location. For further example, an organ removed from an organ donor for later transplantation into a different patient's body (e.g., a liver, kidney, lung, pancreas or heart used in transplant surgery) may be treated before, during, and/or after removal from the organ donor, and may be treated before, during, and/or after its placement in its new location in the patient receiving the organ. The organs may be stored in compositions having features of the invention, such as compositions including an effective dose of a Wnt agent and/or including other therapeutic compounds and agents, as discussed elsewhere in the specification.

Wnt Protein.

Wnt proteins form a family of highly conserved secreted signaling molecules that regulate cell-to-cell interactions during embryogenesis. The terms "Wnts" or "Wnt gene product" or "Wnt polypeptide" when used herein encompass native sequence Wnt polypeptides, Wnt polypeptide variants, Wnt polypeptide fragments and chimeric Wnt polypeptides. In some embodiments of the invention, the Wnt protein comprises palmitate covalently bound to a cysteine residue.

A "native sequence" polypeptide is one that has the same amino acid sequence as a Wnt polypeptide derived from nature. Such native sequence polypeptides can be isolated from cells producing endogenous Wnt protein or can be produced by recombinant or synthetic means. Thus, a native sequence polypeptide can have the amino acid sequence of, e.g. naturally occurring human polypeptide, murine polypeptide, or polypeptide from any other mammalian species, or from non-mammalian species, e.g. *Drosophila, C. elegans*, and the like.

The term "native sequence Wnt polypeptide" includes human and murine Wnt polypeptides. Human wnt proteins include the following: Wnt 1, Genbank reference NP_005421.1; Wnt 2, Genbank reference NP_003382.1, which is expressed in brain in the thalamus, in fetal and adult lung and in placenta; two isoforms of Wnt 2B, Genbank references NP_004176.2 and NP_078613.1. Isoform 1 is expressed in adult heart, brain, placenta, lung, prostate, testis, ovary, small intestine and colon. In the adult brain, it is mainly found in the caudate nucleus, subthalamic nucleus and thalamus. Also detected in fetal brain, lung and kidney. Isoform 2 is expressed in fetal brain, fetal lung, fetal kidney, caudate nucleus, testis and cancer cell lines. Wnt 3 and Wnt3A play distinct roles in cell-cell signaling during morphogenesis of the developing neural tube, and have the Genbank references NP_110380.1 and X56842. Wnt3A is expressed in bone marrow. Wnt 4 has the Genbank reference NP_110388.2. Wnt 5A and Wnt 5B have the Genbank references NP_003383.1 and AK013218. Wnt 6 has the Genbank reference NP_006513.1; Wnt 7A is expressed in placenta, kidney, testis, uterus, fetal lung, and fetal and adult brain, Genbank reference NP_004616.2. Wnt 7B is moderately expressed in fetal brain, weakly expressed in fetal lung and kidney, and faintly expressed in adult brain, lung and prostate, Genbank reference NP_478679.1. Wnt 8A has two alternative transcripts, Genbank references NP_114139.1 and NP_490645.1. Wnt 8B is expressed in the forebrain, and has the Genbank reference NP_003384.1. Wnt 10A has the Genbank reference NP_079492.2. Wnt 10B is detected in most adult tissues, with highest levels in heart and skeletal muscle. It has the Genbank reference NP_003385.2. Wnt 11 is expressed in fetal lung, kidney, adult heart, liver, skeletal muscle, and pancreas, and has the Genbank reference NP_004617.2. Wnt 14 has the Genbank reference NP_003386.1. Wnt 15 is moderately expressed in fetal kidney and adult kidney, and is also found in brain. It has the Genbank reference NP_003387.1. Wnt 16 has two isoforms, Wnt-16a and Wnt-16b, produced by alternative splicing. Isoform Wnt-16B is expressed in peripheral lymphoid organs such as spleen, appendix, and lymph nodes, in kidney but not in bone marrow. Isoform Wnt-16a is expressed at significant levels only in the pancreas. The Genbank references are NP_057171.2 and NP_476509.1.

The term "native sequence Wnt protein" includes the native proteins with or without the initiating N-terminal methionine (Met), and with or without the native signal sequence. The native sequence human and murine Wnt polypeptides known in the art are from about 348 to about 389 amino acids long in their unprocessed form reflecting variability (particularly at the poorly conserved amino-terminus and several internal sites), contain 21 conserved cysteines, and have the features of a secreted protein. The molecular weight of a Wnt polypeptide is about 38-42 kD.

A "variant" polypeptide means a biologically active polypeptide as defined below having less than 100% sequence identity with a native sequence polypeptide. Such variants include polypeptides wherein one or more amino acid residues are added at the N- or C-terminus of, or within, the native sequence; from about one to forty amino acid residues are deleted, and optionally substituted by one or more amino acid residues; and derivatives of the above polypeptides, wherein an amino acid residue has been covalently modified so that the resulting product has a non-naturally occurring amino acid. Ordinarily, a biologically active Wnt variant will have an amino acid sequence having at least about 90% amino acid sequence identity with a native sequence Wnt polypeptide, preferably at least about 95%, more preferably at least about 99%.

A "chimeric" Wnt polypeptide is a polypeptide comprising a Wnt polypeptide or portion (e.g., one or more domains) thereof fused or bonded to heterologous polypeptide. The chimeric Wnt polypeptide will generally share at least one biological property in common with a native sequence Wnt polypeptide. Examples of chimeric polypeptides include immunoadhesins, combine a portion of the Wnt polypeptide with an immunoglobulin sequence, and epitope tagged polypeptides, which comprise a Wnt polypeptide or portion thereof fused to a "tag polypeptide". The tag polypeptide has enough residues to provide an epitope against which an antibody can be made, yet is short enough such that it does not interfere with biological activity of the Wnt polypeptide. Suitable tag polypeptides generally have at least six amino acid residues and usually between about 6-60 amino acid residues.

A "functional derivative" of a native sequence Wnt polypeptide is a compound having a qualitative biological property in common with a native sequence Wnt polypeptide. "Functional derivatives" include, but are not limited to, fragments of a native sequence and derivatives of a native sequence Wnt polypeptide and its fragments, provided that they have a biological activity in common with a corresponding native sequence Wnt polypeptide. The term "derivative" encompasses both amino acid sequence variants of Wnt polypeptide and covalent modifications thereof.

Other activators of wnt signaling include compounds that bind to, and activate receptors of the Frizzled family on the cell surface, e.g. antibodies and fragments thereof, wnt mimetics and derivatives, and the like. An additional method of achieving Wnt inhibition is the neutralization of a Wnt inhibitor, i.e. the chelation of Dkk by a soluble ectodomain of Kremen1/2 or LRP5/6).

Casein kinase Iε (CKIε) has been identified as a positive regulator of the Wnt signaling pathway, for example see Peters et al. (1999) Nature 401:345-350; and Sakanaka et al. (1999) Proc. Natl. Acad. Sci. USA 96:12548-12552.

GSK3β is one of the components of a protein complex that regulates the stability of β-catenin. Phosphorylation of the GSK3β sites in the N terminus of β-catenin is believed to be a signal for degradation. GSK3β has been placed between Dishevelled and β-catenin in the Wnt pathway (Hooper et al. (1994) Nature 372:461-464; Siegfried et al. (1994) Nature 367:76-80). Inhibition of GSK3β activity by lithium salt or GSK3β-binding protein (GBP/FRAT) mimics Wnt signaling. GSK3b inhibitors are known in the art, for examples see Kelly et al. (2004) Exp Neurol. 188(2):378-86; Wan et al. (2004) Chem. Biol. 11(2):247-59; Bhat et al. (2003) J Biol. Chem. (2003) 278(46):45937-45; and Wagman et al. (2004) Curr Pharm Des. 10(10):1105-37.

Biologically Active Wnt. The methods of the present invention in some embodiments will utilize Wnt polypeptide compositions that are active when administered to an animal, e.g. a mammal, in vivo or ex vivo. One may determine the specific activity of a Wnt protein in a composition by determining the level of activity in a functional assay after in vivo administration, e.g. upregulation of stem cell proliferation, β-catenin stabilization, etc., quantitating the amount of Wnt protein present in a non-functional assay, e.g. immunostaining, ELISA, quantitation on coomasie or silver stained gel, etc., and determining the ratio of in vivo biologically active Wnt to total Wnt.

Lipid structures have been found to be important in maintaining the activity of wnt proteins following in vivo administration. The wnt proteins are not encapsulated in the aqueous phase of these structures, but are rather integrated into the lipid membrane, and may be inserted in the outer layer of a membrane.

The methods used for tethering wnt proteins to the external surface of a liposome or micelle may utilize a sequence so as to emphasize the exoliposomal display of the protein, where crude liposomes are first pre-formed; wnt protein is then added to the crude mixture, which will favor addition of exo-liposomal wnt, followed by various formulation steps, which may include size filtering; dialysis, and the like Suitable lipids include fatty acids, neutral fats such as triacylglycerols, fatty acid esters and soaps, long chain (fatty) alcohols and waxes, sphingoids and other long chain bases, glycolipids, sphingolipids, carotenes, polyprenols, sterols, and the like, as well as terpenes and isoprenoids. For example, molecules such as diacetylene phospholipids may find use.

Included are cationic molecules, including lipids, synthetic lipids and lipid analogs, having hydrophobic and hydrophilic moieties, a net positive charge, and which by itself can form spontaneously into bilayer vesicles or micelles in water. The term also includes any amphipathic molecules that can be stably incorporated into lipid micelle or bilayers in combination with phospholipids, with its hydrophobic moiety in contact with the interior, hydrophobic region of the micelle or bilayer membrane, and its polar head group moiety oriented toward the exterior, polar surface of the membrane.

The term "cationic amphipathic molecules" is intended to encompass molecules that are positively charged at physiological pH, and more particularly, constitutively positively charged molecules, comprising, for example, a quaternary ammonium salt moiety. Cationic amphipathic molecules typically consist of a hydrophilic polar head group and lipophilic aliphatic chains. Similarly, cholesterol derivatives having a cationic polar head group may also be useful. See, for example, Farhood et al. (1992) *Biochim. Biophys. Acta* 1111: 239-246; Vigneron et al. (1996) *Proc. Natl. Acad. Sci.* (USA) 93:9682-9686.

Cationic amphipathic molecules of interest include, for example, imidazolinium derivatives (WO 95/14380), guanidine derivatives (WO 95/14381), phosphatidyl choline derivatives (WO 95/35301), and piperazine derivatives (WO 95/14651). Examples of cationic lipids that may be used in the present invention include DOTIM (also called BODAI) (Solodin et al., (1995) Biochem. 34: 13537-13544), DDAB (Rose et al., (1991) BioTechniques 10(4):520-525), DOTMA (U.S. Pat. No. 5,550,289), DOTAP (Eibl and Wooley (1979) Biophys. Chem. 10:261-271), DMRIE (Feigner et al., (1994) J. Biol. Chem. 269(4): 2550-2561), EDMPC (commercially available from Avanti Polar Lipids, Alabaster, Ala.), DCChol (Gau and Huang (1991) Biochem. Biophys. Res. Comm. 179:280-285), DOGS (Behr et al., (1989) Proc. Natl. Acad. Sci. USA, 86:6982-6986), MBOP (also called MeBOP) (WO 95/14651), and those described in WO 97/00241.

While not required for activity, in some embodiments a lipid structure may include a targeting group, e.g. a targeting moiety covalently or non-covalently bound to the hydrophilic head group. Head groups useful to bind to targeting moieties include, for example, biotin, amines, cyano, carboxylic acids, isothiocyanates, thiols, disulfides, α-halocarbonyl compounds, α,β-unsaturated carbonyl compounds, alkyl hydrazines, etc.

Chemical groups that find use in linking a targeting moiety to an amphipathic molecule also include carbamate; amide (amine plus carboxylic acid); ester (alcohol plus carboxylic acid), thioether (haloalkane plus sulfhydryl; maleimide plus sulfhydryl), Schiff's base (amine plus aldehyde), urea (amine plus isocyanate), thiourea (amine plus isothiocyanate), sulfonamide (amine plus sulfonyl chloride), disulfide; hyrodrazone, lipids, and the like, as known in the art.

For example, targeting molecules may be formed by converting a commercially available lipid, such as DAGPE, a PEG-PDA amine, DOTAP, etc. into an isocyanate, followed by treatment with triethylene glycol diamine spacer to produce the amine terminated thiocarbamate lipid which by treatment with the para-isothiocyanophenyl glycoside of the targeting moiety produces the desired targeting glycolipids. This synthesis provides a water soluble flexible linker molecule spaced between the amphipathic molecule that is integrated into the nanoparticle, and the ligand that binds to cell surface receptors, allowing the ligand to be readily accessible to the protein receptors on the cell surfaces.

A targeting moiety, as used herein, refers to all molecules capable of specifically binding to a particular target molecule and forming a bound complex as described above. Thus the ligand and its corresponding target molecule form a specific binding pair.

The term "specific binding" refers to that binding which occurs between such paired species as enzyme/substrate, receptor/agonist, antibody/antigen, and lectin/carbohydrate which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody preferably binds to a single epitope and to no other epitope within the family of proteins.

Examples of targeting moieties include, but are not limited to antibodies, lymphokines, cytokines, receptor proteins such as CD4 and CD8, solubilized receptor proteins such as soluble CD4, hormones, growth factors, peptidomimetics, synthetic ligands, and the like which specifically bind desired target cells, and nucleic acids which bind corresponding nucleic acids through base pair complementarity. Targeting moieties of particular interest include peptidomimetics, peptides, antibodies and antibody fragments (e.g. the Fab' fragment). For example, β-D-lactose has been attached on the surface to target the aloglysoprotein (ASG) found in liver cells which are in contact with the circulating blood pool.

Cellular targets include tissue specific cell surface molecules, for targeting to specific sites of interest, e.g. neural cells, liver cells, bone marrow cells, kidney cells, pancreatic cells, muscle cells, and the like. For example, nanoparticles targeted to hematopoietic stem cells may comprise targeting moieties specific for CD34, ligands for c-kit, etc. Nanoparticles targeted to lymphocytic cells may comprise targeting moieties specific for a variety of well known and characterized markers, e.g. B220, Thy-1, and the like.

The use of liposomes or micelles as a delivery vehicle is one method of interest. A liposome is a spherical vesicle with a membrane composed of a phospholipid bilayer. Liposomes can be composed of naturally-derived phospholipids with mixed lipid chains (like egg phosphatidylethanolamine), or of pure surfactant components like DOPE (dioleolylphosphatidylethanolamine). Liposomes often contain a core of encapsulated aqueous solution; while lipid spheres that contain no aqueous material are referred to as micelles. As the wnt proteins are present in the lipid phase and not the encapsulated aqueous phase, micelles may be used interchangeably with liposome for the compositions of the present invention. The lipids may be any useful combination of known liposome or micelle forming lipids, including cationic lipids, such as phosphatidylcholine, or neutral lipids, such as cholesterol, phosphatidyl serine, phosphatidyl glycerol, and the like.

In another embodiment, the vesicle-forming lipid is selected to achieve a specified degree of fluidity or rigidity, to control the stability of the structure in serum, etc. Liposomes having a more rigid lipid bilayer, or a liquid crystalline bilayer, are achieved by incorporation of a relatively rigid lipid, e.g., a lipid having a relatively high phase transition temperature, e.g., up to 60° C. Rigid, i.e., saturated, lipids contribute to greater membrane rigidity in the lipid bilayer. Other lipid components, such as cholesterol, are also known to contribute to membrane rigidity in lipid bilayer structures. Lipid fluidity is achieved by incorporation of a relatively fluid lipid, typically one having a lipid phase with a relatively low liquid to liquid-crystalline phase transition temperature, e.g., at or below room temperature.

The liposomes may be prepared by a variety of techniques, such as those detailed in Szoka, F., Jr., et al., Ann. Rev. Biophys. Bioeng. 9:467 (1980). Typically, the liposomes are multilamellar vesicles (MLVs), which can be formed by simple lipid-film hydration techniques. In this procedure, a mixture of liposome-forming lipids of the type detailed above dissolved in a suitable organic solvent is evaporated in a vessel to form a thin film, which is then covered by an aqueous medium. The lipid film hydrates to form MLVs, typically with sizes between about 0.1 to 10 microns.

The liposomes micelles, etc. of the invention may have substantially homogeneous sizes in a selected size range, typically between about 0.01 to 0.5 microns, more preferably between 0.03-0.40 microns. One effective sizing method for REVs and MLVs involves extruding an aqueous suspension of the liposomes through a series of polycarbonate membranes having a selected uniform pore size in the range of 0.03 to 0.2 micron, typically 0.05, 0.08, 0.1, or 0.2 microns. The pore size of the membrane corresponds roughly to the largest sizes of liposomes produced by extrusion through that membrane, particularly where the preparation is extruded two or more times through the same membrane. Homogenization methods are also useful for down-sizing liposomes to sizes of 100 nm or less.

The pharmaceutical compositions of the present invention also comprise a pharmaceutically acceptable carrier. Many pharmaceutically acceptable carriers may be employed in the compositions of the present invention. Generally, normal saline will be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc. These compositions may be sterilized by conventional, well known sterilization techniques. The resulting aqueous solutions may be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc.

The concentration of lipid structures in the carrier may vary. Generally, the concentration will be about 0.1 to 1000 mg/ml, usually about 1-500 mg/ml, about 5 to 100 mg/ml, etc. Persons of skill may vary these concentrations to optimize treatment with different lipid components or of particular patients.

Compositions will comprise a therapeutically effective in vivo dose of a wnt protein, and may comprise a cocktail of one or more wnt proteins.

The subject methods are useful for both prophylactic and therapeutic purposes. Thus, as used herein, the term "treating" is used to refer to stabilization of implants, prevention of implant failure, and treatment of a pre-existing condition. Evidence of therapeutic effect may be any diminution in the severity of disease. The therapeutic effect can be measured in terms of clinical outcome or can be determined by immunological or biochemical tests. Patents for treatment may be mammals, e.g. primates, including humans, may be laboratory animals, e.g. rabbits, rats, mice, etc., particularly for evaluation of therapies, horses, dogs, cats, farm animals, etc.

The dosage of the therapeutic formulation will vary widely, depending upon the nature of the condition, the frequency of administration, the manner of administration, the clearance of the agent from the host, and the like. The initial dose can be larger, followed by smaller maintenance doses. The dose can be administered as infrequently as weekly or biweekly, or more often fractionated into smaller doses and administered daily, semi-weekly, or otherwise as needed to maintain an effective dosage level.

In some embodiments of the invention, administration of the wnt pharmaceutical formulation is performed by local administration. Local administration, as used herein, may refer to topical administration, but more often refers to injection or other introduction into the body at a site of treatment. Examples of such administration include injection at the site of an implant or bone weakness, and the like. It is found that the lipid structures of the present invention generally are less effective when systemically administered, and the highest activity may be found at or around the site where it is initially introduced.

In some embodiments of the invention, the formulations are administered on a short term basis, for example a single administration, or a series of administration performed over, e.g. 1, 2, 3 or more days, up to 1 or 2 weeks, in order to obtain a rapid, significant increase in activity. The size of the dose administered must be determined by a physician and will depend on a number of factors, such as the nature and gravity of the disease, the age and state of health of the patient and the patient's tolerance to the drug itself.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. Due to biological functional equivalency considerations, changes can be made in protein structure without affecting the biological action in kind or amount. All such modifications are intended to be included within the scope of the appended claims.

EXPERIMENTAL

Example 1

Wnt/β-Catenin Protects Against Hypoxia-Induced Liver Injury in Mice Through Augmented HIF-1 Signaling The Wnt signaling pathway is an established critical molecular regulator of hepatic development, regeneration and carcinogenesis. The canonical Wnt signal transduction pathway is regulated through post-translational modifications of the β-catenin protein. Wnt signaling is initiated through Wnt ligand binding to two membrane bound receptors, Frizzled, and the co-receptor Lipoprotein receptor Related Proteins 5 and 6 (LRP-5/6). In the absence of Wnt, cytoplasmic β-catenin is phosphorylated by the Axin/APC/GSK3β complex and then degraded by the ubiquitin/proteasome system. In the presence of extracellular Wnt ligand, β-catenin is dephosphorylated via N-terminal serine/threonine residues allowing stabilized β-catenin to accumulate and translocate to the nucleus where it activates the transcription complex T cell factor/lymphoid enhancer factor (TCF/LEF).

Recently, additional post-translational modifications of β-catenin have been described that significantly affect its subsequent activity as a transcriptional regulator. Specifically, acetylation of lysine residues located in the armadillo repeats of β-catenin by the transcriptional co-activator p300/CBP (CREB-binding protein) family members leads to enhanced β-catenin/TCF signal transduction. Moreover, the stress-responsive deacetylase, Sirtuin1 (Sirt1), has been shown to counteract the effects of p300/CBP on β-catenin resulting in a significant attenuation in TCF signal transduction. Although the biologic effect of Wnt signaling is classically regarded as a critical cellular mitogen, morphogen and motogen, emerging evidence suggests an additional novel role in modulating cell survival.

Recently, alternative β-catenin signal transduction pathways that may play a significant role in adaptation to oxidative stress have been described. In vitro evidence in human colorectal carcinoma and embryonic kidney cells has been previously provided suggesting that β-catenin can be diverted as a transcriptional activator from TCF/LEF to adaptive pathways like HIF-1 (hypoxia inducible factor-1) in order to mediate the cellular response to oxidative stress. HIF-1, a key regulator of the cellular response to hypoxia, is a heterodimer consisting of a hypoxia-stabilized α-subunit (HIF-1α) and a constitutively expressed β-subunit (HIF-1β). Under hypoxic conditions, stabilized HIF-1α translocates to the nucleus, dimerizes with HIF-β and binds hypoxia response elements (HRE) to activate target genes to promote angiogenesis and cellular metabolic changes.

Since both HIF and Wnt signaling have established roles in regulating cell metabolism and survival, we questioned whether β-catenin is required for an effective response to hypoxic injury in the highly metabolically active liver. The present study was designed to investigate the role of Wnt signaling in the hepatocyte response to hypoxia-induced stress. Herein, we demonstrate that liver-specific β-catenin deficient mice (LT2 KD) are significantly more sensitive to liver ischemia-reperfusion injury (IRI) resulting in severe necrosis and apoptosis. Evidence is provided that the observed enhanced hypoxic liver injury is related to reduced HIF-1 signaling in the absence of β-catenin. Conversely, we show that in mice with conditional Wnt/β-catenin stabilization, there is strong hepatic resistance to hypoxia and IRI. Moreover, we provide evidence that the molecular mechanism by which β-catenin regulates hypoxic injury protection in the liver is mediated by redox balance yielding a β-catenin switch from binding TCF to complex with HIF-1 for cell adaptation and survival under hypoxic stress. We further show that hepatocyte oxidative injury disrupts β-catenin/TCF signaling through Sirt1 directed deacetylation of β-catenin and that deacetylated β-catenin complexes with HIF-1 in response to injury. Together, these data provide the first in vivo evidence that β-catenin is a key component of an effective, tissue specific, hypoxia response and that the molecular mechanism is mediated by cellular redox balance and post-translational changes in β-catenin.

Results

Oxidative Stress Inhibits β-Catenin/TCF Signaling in Hepatocytes.

Figure 1A:
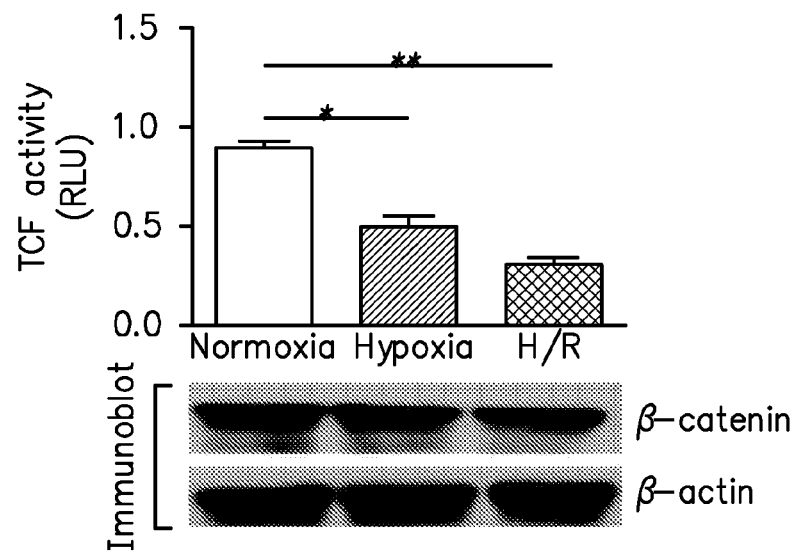
FIG. 1. β-catenin/TCF signaling is impacted by cellular redox changes.
  (A) β-catenin/TCF reporter activity significantly decreases in response to 1% hypoxia for 24 hours or H/R (24/2 hours) in AML12 hepatocytes without a change in total β-catenin protein.
  (B) Intracellular ROS levels in AML12 hepatocytes are significantly elevated by hypoxia as measured by DCF-DA flow cytometry. One hour pre-treatment with NAC (2 mmol/L) significantly prevents ROS production under hypoxia.
  (C) One hour pre-treatment with NAC (2 mmol/L) prevents hypoxia-induced inhibition of β-catenin/TCF signaling in AML12 hepatocytes. RLU=relative light units. *p<0.05, **p<0.01.
Figure 1B:
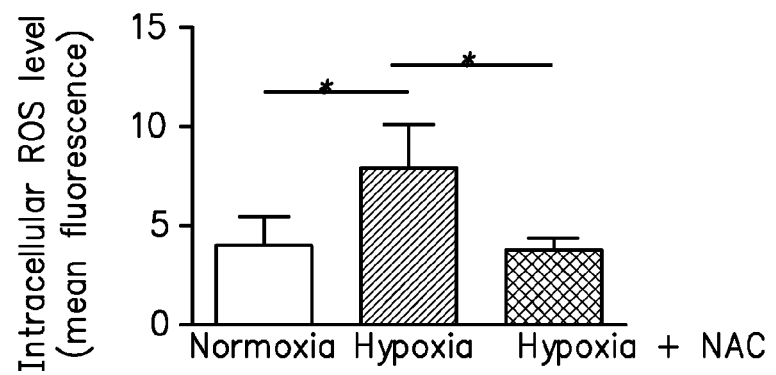
Figure 1C:
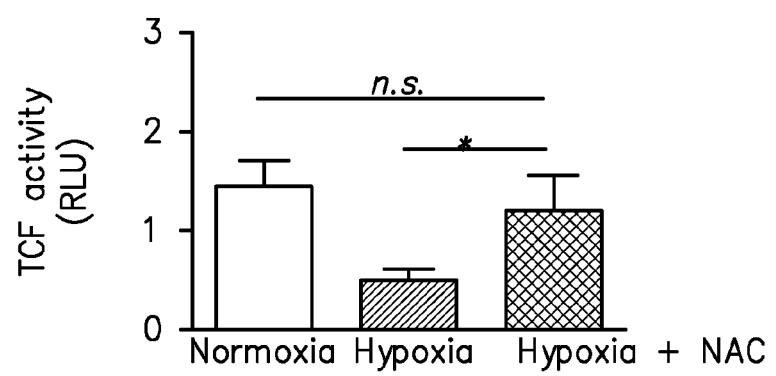

Since Wnt/β-catenin signaling and cellular redox balance are integral to liver homeostasis, we sought to determine the effect of reactive oxygen species (ROS) on Wnt signaling in hepatocytes. As shown in FIG. 1A, the mouse hepatocyte cell line AML12 was treated in vitro by three different oxidative stimuli as indicated. Exposure to each oxidant resulted in a uniform and significant decrease in β-catenin/TCF reporter activity (FIG. 1A) that was most pronounced in response to hypoxia. The inhibition of β-catenin/TCF signal transduction occurred without a change in total β-catenin protein (FIG. 1A) or transcript level. Moreover, the serine-37/threonine-41 phosphorylation status of β-catenin did not change in response to hypoxia. However, the expression level of transcripts for the β-catenin/TCF target genes, Cyclin D1, c-Myc and Axin2, were significantly reduced in response to hypoxia (FIG. 1B) in-line with the signal activity repression observed by reporter assay (FIG. 1A). Furthermore, the hypoxia-induced reduction in TCF signaling appeared to be ROS dependent as the antioxidant N-acetylcysteine (NAC), a ROS scavenger, was able to decrease intracellular ROS (FIG. 10) and diminish the suppressive effect of hypoxia derived ROS on β-catenin/TCF signal transduction (FIG. 1D). These data demonstrate that β-catenin signal transduction is significantly impacted by cellular redox balance.

Conditional β-Catenin Knockdown Sensitizes Mice to Hypoxic Liver Injury.

Previous studies have reported heightened hepatic sensitivity to a variety of injury stimuli in the absence β-catenin although the response to an acute oxidative stimulus and hypoxic injury has not been evaluated. In order to determine β-catenin's role in the adaptive response to hypoxic injury in vivo, we developed a novel mouse model for the conditional and regulatable genetic deletion of β-catenin from hepatocytes in order to overcome any compensatory changes that may occur when β-catenin is deleted during development in cells with transcriptionally active albumin (Alb-Cre) as previously reported. The triple transgenic mouse LAP-tTa/tetO-Cre/β-catenin$^{loxP2}$ (subsequently abbreviated LT2) was engineered to effect the conditional deletion of β-catenin from mature hepatocytes in response to the tetracycline transactivating system as described above and previously (FIG. 2A, B). Quantitative real-time PCR verified the efficient reduction (70%) of β-catenin expression in the LT2 knockdown mouse (FIG. 2C). In order to determine if β-catenin knockdown exacerbates hypoxic oxidative injury in vivo, we subjected LT2 knockdown mice and their wild-type littermates to partial warm liver ischemia for 75 minutes followed by 6 hours of reperfusion (ischemia-reperfusion injury). Liver samples and blood were harvested at the indicated time points for analysis. Liver injury, as assessed by serum alanine aminotranferase (ALT) and aspartate aminotransferase (AST), was significantly increased in LT2 mice after IRI (FIG. 2D). Similarly, wild-type mice subjected to IRI showed an increase in transaminases compared to sham operated wild-type mice, but had a 6-fold less elevation in ALT and 4-fold less elevation in AST, when compared to LT2 knockdown mice (FIG. 2D). Hematoxylin and Eosin staining after IRI showed increased hepatocellular injury with necrosis, congestion and swelling in LT2 hepatocytes as compared to wild-type mice (FIG. 2E). In contrast, wild-type livers showed relatively well-preserved histological architecture without definitive necrosis. DHE staining for the in situ detection of ROS revealed a pronounced increase in the LT2 mouse liver as compared to control liver after IRI. Western blot analysis (FIG. 2F) for apoptosis specific cleavage of the hepatic Keratin 18 (K18Asp237) revealed that β-catenin knockdown mice are more susceptible to hepatocellular apoptosis during IRI. In line with the reduction in β-catenin, mRNAs for Cyclin D1, c-Myc and Axin2, known transcriptional targets of β-catenin/TCF, were also uniformly reduced in the absence of β-catenin after IRI. Intriguingly, a corresponding and significant reduction in the expression of the HIF target genes, cyclooxygenase2 (Cox2), inducible nitric-oxide synthase (iNOS) and erythropoietin (Epo), was also observed in β-catenin deficient hepatocytes compared to WT in response to hypoxia (FIG. 2G). As evidence of increased hepatocellular oxidative injury and in support of a β-catenin/HIF-1 specific deficit, β-catenin deficient hepatocytes showed a uniform induction of the compensatory anti-oxidant genes (glutathione S-transferase (GST), superoxide dismutase 1 (SOD1) and glutathione peroxidase 1 (GPX1)) in the LT2 mice after IRI.

As the potential for crosstalk between β-catenin and HIF-1 has been previously demonstrated, we sought to further investigate the basis for the interaction between β-catenin and TCF or HIF signal activity in response to hypoxic stress. In vitro, β-catenin deficient hepatocytes demonstrated reduced TCF and HIF-1 signaling in response to hypoxia (FIG. 3A, 3B). As a result of decreased TCF and HIF signal transduction, primary hepatocytes with β-catenin knockdown showed increased apoptosis as measured by a significant increase in cleaved K18. To further elucidate, whether the protective effect against hypoxia-induced apoptosis is specific to HIF-1 signaling, hepatocytes were treated with YC-1 [3-(5'-hydroxymethyl-2'-furyl)-1-benzylindazole], a known HIF-1 inhibitor. HIF-1 inhibition by YC-1 under hypoxia significantly reduced HRE activity (see supplementary data S4) and induced significant apoptosis (FIG. 3C). Together, these results demonstrate that β-catenin has a protective role in hypoxic liver injury through augmenting HIF-1 signaling that dramatically reduces the degree of hepatocellular ischemia-reperfusion injury in vivo in a β-catenin dependent manner.

Augmented β-Catenin/TCF Signaling Protects Mice from Liver IRI In Vivo.

Figure 4A:
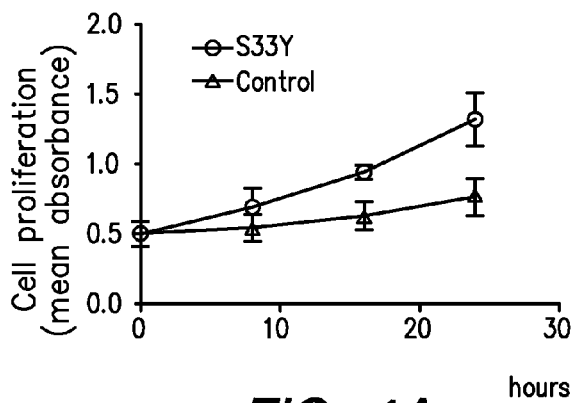
Figure 4B:
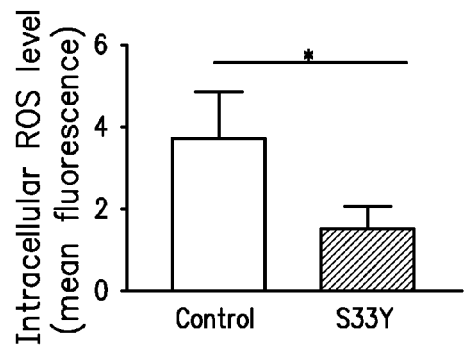
Figure 4C:
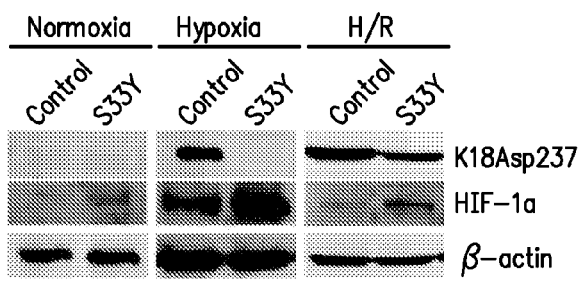
Figure 4D:
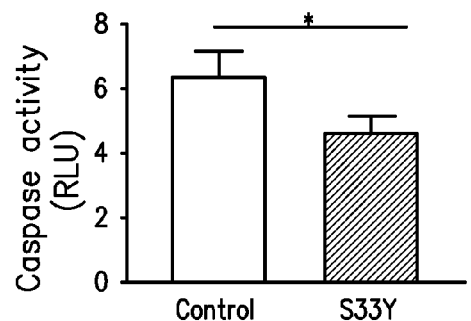
Figure 4E:
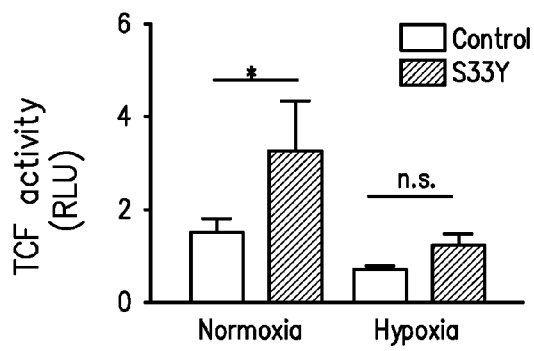
Figure 4F:
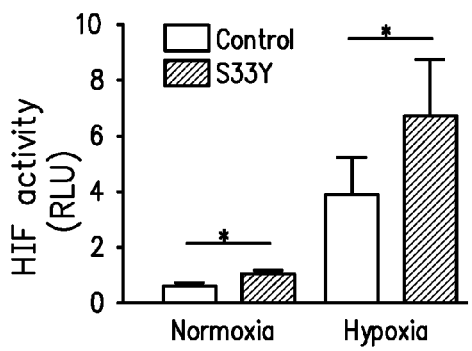

To further investigate if β-catenin signaling plays a role in hypoxic injury protection in vivo, we created a novel, hepatocyte-specific Wnt1 transgenic mouse for the regulatable overexpression of Wnt as described above. This double transgenic mouse (CEBP/β-tTa/tetO-Wnt1-Luc) (subsequently abbreviated Wnt1+) enables hepatocyte-specific activation of the transgene Wnt1-Luc in response to Doxycycline (Dox−) and facilitates monitoring of expression by bioluminescence imaging (BLI). In response to Wnt1 over-expression, a significant increase in the canonical β-catenin target gene, Cyclin D1, as well as a moderate increase in total β-catenin protein level in the Wnt1+ hepatocytes was observed (FIG. 4A). In line with these findings, TCF and HIF reporter activity (FIG. 4A, 4B) as well as β-catenin target genes were all correspondingly significantly increased in Wnt1+ hepatocytes. In order to determine if Wnt mediated β-catenin gain of function has a protective effect against hypoxic injury in vivo, we subjected Wnt1+ mice (Dox−) and wild-type (Dox+) littermates to IRI. Liver transaminases were significantly less elevated in Wnt1+ mice following IRI indicating significant increased resistance to oxidative injury in vivo (FIG. 4C). Conversely, wild-type mice without Wnt1 over-expression and subjected to IRI showed a 4-fold increase in ALT and 5-fold elevation in AST compared to Wnt1+ mice (FIG. 4C). Hematoxylin and Eosin staining in wild-type livers showed congestion and degenerative changes including hepatocyte ballooning, indistinct cytoplasmic borders and cytoplasmic vacuolization (FIG. 4D). In contrast, the hepatocellular architecture in Wnt1+ livers was well preserved and did not show significant degenerative injury. Corresponding to the elevation in transaminases, Wnt1+ mice were also more resistant to hypoxia-induced hepatocyte apoptosis (FIG. 4E) as measured by changes in cleaved Keratin18 levels. Intriguingly and in contrast to the results with β-catenin knockdown, mRNA levels for the HIF target genes, Cox2, Glut1 (glucose transporter 1), iNOS (inducible nitric-oxide synthase) and VEGF (vascular endothelial growth factor), were uniformly increased in Wnt1+ liver compared to wild-type littermates in response to hepatic IRI (FIG. 4F). This augmented response in HIF target gene expression is a likely significant contributor to the observed increase in hepatocyte resistance to hypoxic injury. In further support of a Wnt1 mediated increase in resistance to oxidative injury, a uniform decrease in the anti-oxidant genes SOD1 and GPX1 was also observed following IRI in the transgenic livers compared to wild-type (FIG. 4G). Taken together, this data demonstates that Wnt1 overexpression confers a significant increase in hepatic protection against hypoxic IRI through augmented HIF-1 signaling and an overall reduction in redox imbalance.

Hepatocytes Overexpressing β-Catenin are More Resistant to Hypoxia-Induced Apoptosis by Augmented HIF-1 Signaling.

Figure 5A:
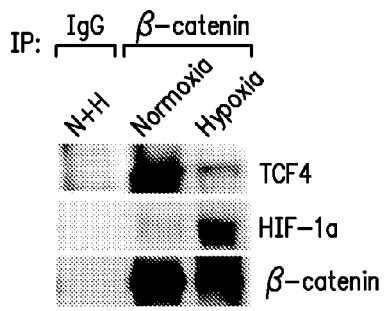
Figure 5B:
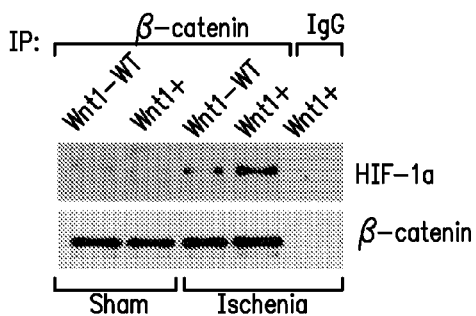
Figure 5C:
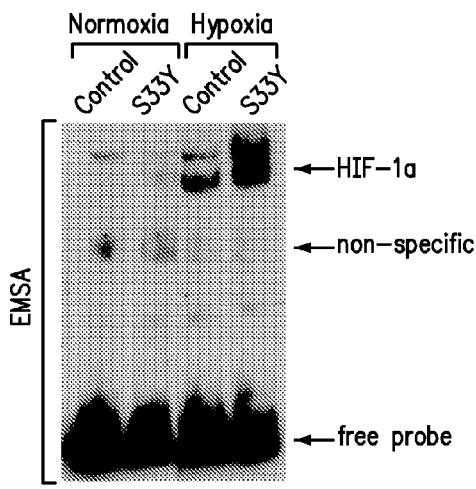
Figure 5D:
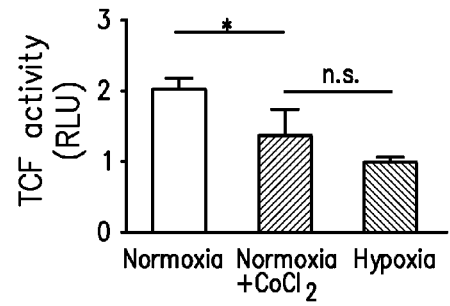
Figure 5D:
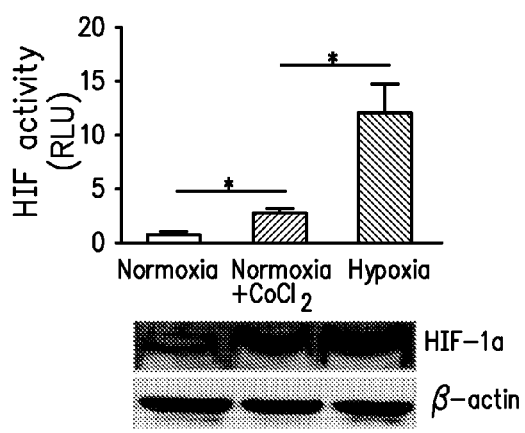

In order to further investigate the specific role of β-catenin in the hepatocyte response to hypoxic injury, a hepatocyte cell line (AML12) carrying an amino terminus phosphorylation resistant point mutation (S33Y) that renders constitutive β-catenin protein stabilization independent of GSK3β was created. Phosporylation resistant β-catenin mutants demonstrated increased total β-catenin protein level, robust TCF signal transduction (FIG. 5A) and an increased rate of proliferation compared to control cells. When cells were exposed to hypoxic stress, β-catenin gain of function cells displayed reduced sensitivity to oxidative stress with less apoptosis and lower ROS levels compared to control (FIG. 5B, 5C). MTT assay revealed that β-catenin mutants continued to proliferate and demonstrate death resistance despite hypoxic injury (FIG. 5D). Taken together, this data confirmed that β-catenin stabilization protects hepatocytes against hypoxic injury by preventing apoptosis and increasing cell survival.

Figure 5E:
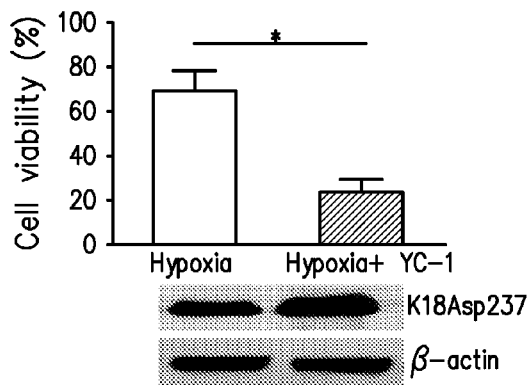

The findings above that β-catenin/TCF signaling is inhibited in response to ROS and hypoxia (FIG. 1A), and effective HIF signaling is in part dependent on β-catenin and thereby required for hepatocyte resistance to hypoxia, lead us to further explore the mechanism by which β-catenin affords increased protection against hypoxic injury. When β-catenin mutants and control cells were exposed to hypoxia, TCF signaling was decreased to a comparable degree as control cells despite a higher baseline elevation in the mutant cells (FIG. 5E). Heightened TCF activity was also reflected by an increase in transcriptional β-catenin target gene expression. When exposed to hypoxia, HIF-1 activity increased in both control and mutant cells (FIG. 5F). Interestingly, β-catenin mutants also demonstrated a significantly increased HIF-1 transcription activity compared to control cells (FIG. 5F). Finally, in order to determine whether the Wnt mediated increase in HIF signaling is dependent on β-catenin/TCF signaling, β-catenin binding to TCF was blocked using a dominant negative construct (dnTCF4). Remarkably, when β-catenin is prevented from binding TCF in hepatocytes, the HIF-1 response by reporter assay is profoundly increased under hypoxia (5G). These results support the in vivo findings above and further extend these findings to demonstrate that Wnt augmented HIF signaling occurs with β-catenin stabilization, yet independent of the canonical β-catenin/TCF pathway and that the ROS mediated dampening of β-catenin/TCF signaling is not dependent on phosphorylation of β-catenin.

In Response to Hypoxia β-Catenin Diverts from TCF Binding to HIF-1 to Support Cell Survival.

Figure 6A:
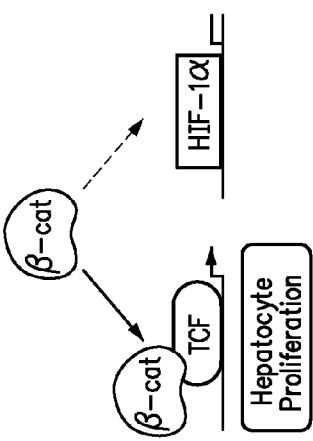
Figure 6B:
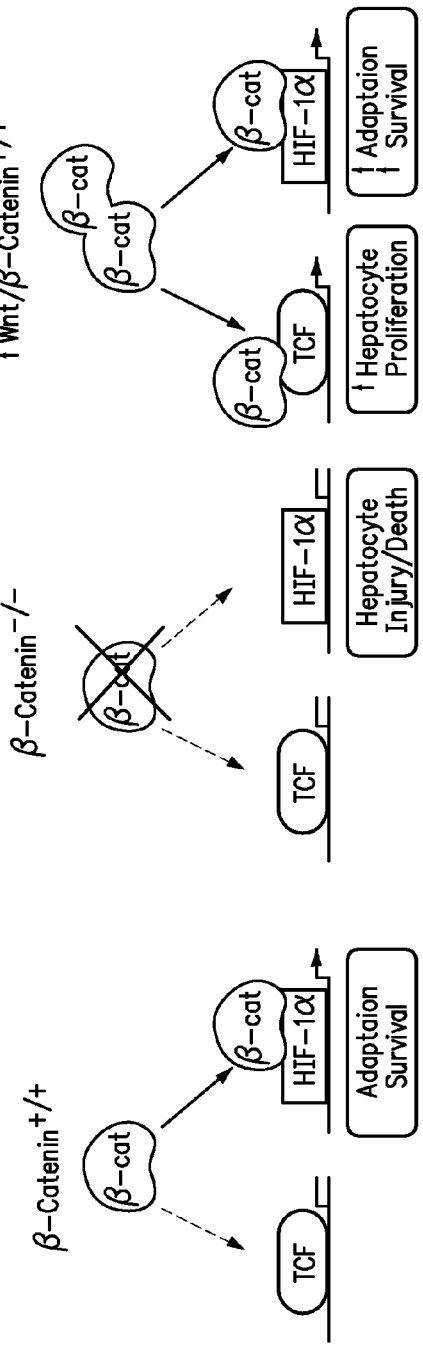

Given the findings above, we next sought evidence to confirm whether β-catenin complexes directly with TCF and or HIF-1 according to cellular conditions that may favor either proliferation or survival respectively. In order to investigate whether the inhibition of TCF signaling is a result of a β-catenin switch as a transcriptional activator, co-immunoprecipitation assays using the human hepatocellular carcinoma cell lines Huh7 and HepG2 cells was performed. As demonstrated in FIG. 6, β-catenin primarily complexes with TCF under normoxia and alternatively primarily binds HIF-1 in response to hypoxia (FIG. 6A). In order to investigate if β-catenin/TCF signaling can be dampened by HIF-1 directly, we stabilized the expression of HIF-1α under normoxia by the HIF mimetic cobalt chloride ($CoCl_2$) (FIG. 6B). In the presence of stabilized HIF under normoxic conditions, there was a significant reduction in TCF signal transduction in hepatocytes (FIG. 6B) comparable to the inhibition observed under hypoxia.

β-Catenin is Deacetylated in Response to Hypoxia.

Since TCF signaling is inhibited under hypoxia (FIG. 1A) independent of a change in either total β-catenin transcript or protein level (FIG. 1A), as well as independent of GSK3β-phosphorylation changes, we questioned whether alternate post-translational changes involved in β-catenin (i.e. acetylation) signaling is the governing modification in the hepatocyte stress response. Since Sirt1, a known histone deacetylase (HDAC), has been linked to increased stress resistance and can directly deacetylate β-catenin, we sought to further determine whether hypoxia would induce Sirt1 expression and consequently whether Sirt1 could inhibit βcatenin/TCF signal transduction. Immunoblot revealed a significant induction of Sirt1 expression and a significant decrease in acetylated β-catenin lysine residues (FIG. 7A) in hepatocytes exposed to hypoxia. To further investigate the role of Sirt1 on β-catenin/TCF signaling, shRNA to Sirt1 was utilized to manipulate its expression level. As shown in FIG. 7B, under hypoxia, β-catenin/TCF signal activity remained significantly higher in Sirt1 knockdown cells as compared to controls. In addition, while Sirt1 is induced and TCF signaling is suppressed under hypoxia (FIG. 7C), the pharmacological modulation of Sirt1 through the addition of its inhibitor nicotinamide (NAM) abolished this effect (NAM inhibits NAD activity that is required for the enzymatic activity of Sirt1) (FIG. 7C). In contrast, the Sirt1 agonist resveratrol, significantly inhibited β-catenin/TCF signal transduction (FIG. 7D). These findings were further supported by maintained β-catenin target gene expression (Cyclin D1, c-Myc and Axin2) under hypoxia in Sirt1 deleted cells (FIG. 7E). This effect corresponded to a significant repression of transcripts for the HIF target genes iNOS and Cox2 under hypoxia and in the absence of Sirt1 (FIG. 7F). Taken together, these results show that Sirt1 can dynamically modulate β-catenin's function as a transcriptional co-activator in response to hypoxia through a likely mechanism of β-catenin deacetylation.

The hepatocellular injury response to a variety of stimulants involving oxidative stress is a common mechanism in nearly all liver pathologies. In this study we utilized cellular hypoxia and tissue ischemia-reperfusion injury as clinically relevant models involving profound changes in hepatocyte redox balance to gain a better understanding of critical molecular regulators of hepatic adaptation and potential liver protection strategies. As tissue hypoxia and Wnt signaling are both known to be critical mediators of diverse biologic processes from development to tissue regeneration and tumorigenesis, the findings reported herein have far reaching implications for developing novel treatment strategies.

These data demonstrates that Wnt/β-catenin can critically modulate an effective HIF-1 response in vivo. The findings demonstrate that HIF signaling is specifically impaired and cellular redox balance disrupted as a result of β-catenin depletion from hepatocytes. β-catenin signal transduction is significantly impacted by cellular redox balance as shown by changes in ROS level and their modulation by the anti-oxidant NAC. In response to changes in cellular redox balance, we have shown that β-catenin/TCF signaling is reduced without a significant change in either total β-catenin protein or critical amino-terminus phosphorylation changes that are the target of GSK3β for physiologic control. Taken together, our results demonstrate that an increase in cellular ROS levels that accompany numerous injury stimuli (oxidative, hypoxic, metabolic and genotoxic stress), and thereby relevant hepatic pathologic states, are critical intra-cellular mediators of β-catenin signal transduction in response to changing conditions. This provides a key mechanistic distinction to deepen our understanding of the proposed model (FIG. 9) in which cells (hepatocytes) respond to changes in relevant stimuli to enact programs alternatively for proliferation (TCF) when conditions are favorable, or adaptation and survival (HIF) in response to limiting environmental conditions.

The findings in this study are the first to demonstrate that HIF signaling can be enhanced through Wnt pathway manipulation in order to realize increased cell survival in response to hypoxia in vivo. These findings are of significant importance for developing strategies to support cellular and organ transplantation, in cancer treatment, tissue protection or regeneration.

In summary, this study provides the first in vivo evidence that β-catenin is a key component of an effective tissue specific hypoxia response and that the molecular mechanism is mediated by cellular redox balance and post-translational changes in β-catenin. Our observations have significant clinical relevance since hypoxia is a common feature of many liver diseases. In light of the data presented here, this study may further support the promise and clinical application of Wnt1 manipulation or other modulators of Wnt/β-catenin signal activation in clinically relevant settings involving a hepatic oxidative stress response to effect hepatic injury protection, repair and regeneration.

Materials and Methods

Animals.

In order to investigate the role of Wnt signaling in hypoxia adaptation in the liver, two separate and conditional, hepatocyte-specific mouse models were created: a β-catenin knockdown mouse and a Wnt1 overexpression mouse, both utilizing a tetracycline transactivating (tTa) system. For the β-catenin knockdown mouse, a previously described mouse possessing the liver enriched activator (LAP) promoter CEBP/β driving tTa was bred to a mouse possessing a tetracycline response element driving Cre (tetO-Cre). Subsequent progeny were further bred to the previously described β-cateninloxP2 mouse. Several crosses were completed to achieve a stable strain that is fertile and normal in appearance and liver-body weight (LBW) in the absence of transgene activation (CRE) by Dox withdrawal. The resultant triple transgenic mouse LAP-tTa-tetO-Cre-β-cateniex$^{loxP2}$ (subsequently abbreviated LT2) demonstrated both in vitro and in vivo responsiveness to the tetracycline analog Doxycycline for β-catenin deletion.

For the conditional Wnt1 overexpression mouse, a tetracycline-responsive tetO-Wnt1.Luc mouse as previously described was crossed to a mouse bearing the liver-specific CEBP/β promoter driving expression of the tetracycline transactivator tTa (LAP-tTa) as described elsewhere. This double transgenic mouse (CEBP/β-tTa/tetO-Wnt1-Luc) (subsequently abbreviated Wnt1+) enables hepatocyte-specific activation of the transgene Wnt1-Luc in a Doxycycline (Dox−) dependent manner and facilitates monitoring of expression by bioluminescence imaging (BLI).

For the following experiments sex-matched, 8-12 weeks old littermates were used. All experiments using animals were performed in accordance with Stanford University Animal Care and Use Committee Guidelines. All animal studies were conducted under a protocol approved by the Stanford University School of Medicine Institutional Animal Care and Use Committee and in strict accordance with National Institute of Health (NIH) guidelines.

Liver IRI Model.

We used a murine model of 70% partial warm hepatic ischemia-reperfusion injury (IRI) as previously described. Each treatment group consisted of at least 5 animals. Briefly, mice were anesthetized with isoflurane, midline laparotomy was performed and an atraumatic clip was used to interrupt the arterial and portal venous blood flow to left lateral and median lobes. After 90 minutes of ischemia, the clip was removed initiating hepatic reperfusion and the abdominal cavity was closed. Mice were sacrificed at 6 hours of reperfusion, after which blood was collected from the heart and the liver lobes were removed and further processed.

Hepatocellular Function.

Serum alanine aminotranferase (ALT) and aspartate aminotransferase (AST) levels were used as established markers of hepatocyte injury. At 6 hours after reperfusion following 90 minutes of ischemia, blood samples were obtained via cardiac puncture, immediately centrifuged at 3000 g for 10 minutes, and stored at −80° C. until analysis. Serum ALT and AST were measured using a standard clinical automatic analyzer.

Histology.

For histological analysis, tissue samples were fixed in 4% formaldehyde/phosphate-buffered saline overnight at 4° C. The samples were dehydrated and embedded in paraffin. Liver paraffin sections (5 μm thick) were stained with hematoxylin-eosin. The severity of liver IRI (necrosis, sinusoidal congestion and centrilobular ballooning) was analyzed by a pathologist.

Primary Hepatocyte Culture.

Hepatocytes from 10-12 week old mouse livers (n=3) were isolated using the two-step collagenase perfusion as described previously (60). Cells were seeded in wells pre-coated with collagen at a density of 100,000 cells/ml in Dulbecco's minimal essential medium (DMEM)/F12 supplemented with 10% fetal bovine serum (FBS)(29, 61). After 6 hours, media was changed to reduced serum media containing 1% FBS and hepatocytes were cultured up to 72 hours.

Cell Culture.

The differentiated non-transformed mouse hepatocyte cell line AML12 (ATCC Inc.) was cultured in Dulbecco's minimal essential medium (DMEM)/F-12 media (1:1) supplemented with 10% fetal bovine serum (FBS), 1% penicillin-streptomycin antibiotics and 5 μg/ml insulin, 5 μg/ml transferrin, 5 ng/ml selenium as previously described (62). The human hepatocellular carcinoma cell lines Huh7 and HepG2 were grown in DMEM media containing 10% FBS and 1% penicillin-streptomycin antibiotics. Media was purchased from Hyclone (Logan, Utah). All other medium components were purchased from Invitrogen (Carlsbad, Calif.). Cultures were maintained at 37° C. in a hunified 5% $CO_2$ atmosphere. For hypoxic conditions, cells were grown at 1% $O_2$ in a custom-designed incubator (XVivo Hypoxia Chamber; BioSpherix) for 24 hrs.

Small Hairpin RNAs, Plasmids and Transfection.

To activate canonical Wnt signaling through TCF, we utilized the plasmid, pcDNA3S33Y, which contains mutant β-catenin with flag tag at its C-terminal. In brief, stable mutants conferring β-catenin gain of function were derived through stable retroviral transfection and neomycin selection. The β-catenin N-terminus (aa31 to 47) contains the GSK3β phosphorylation sites that regulate β-catenin ubiquitin mediated degradation. Previous mutational analysis has demonstrated that a mis-sense mutation of tyrosine for serine at codon 33 (S33Y) results in robust TCF dependent transcriptional activation of up to 12 fold over basal and wild-type β-catenin directed TCF activation. Moreover, the S33Y β-catenin (β-catenin$^{\Delta S33Y}$) mutant protein accumulates confirming that post-translational modifications of the N-terminus phosphorylation sites direct β-catenin stabilization as previously described.

To inhibit canonical β-catenin/TCF signaling in hepatocytes, mutant TCF4 (aa31) lacking the β-catenin binding domain at the TCF4 N-terminus was used. Mutant TCF4 retain DNA binding activity and thus function in a dominant negative fashion. In brief, we utilized a retroviral expression vector containing a mutant dnTCF4 expression cassette upstream of a neomycin resistance gene as previously described.

For lentiviral production, 293T cells were transfected with the Sirt1 shRNA plasmid simultaneously with packaging plasmids CMV and VSV-G. The media containing the progeny virus released for the 293T cells was collected and used to infect the cells for 24-48 hours in the presence of 8 μg/ml polybrene (Sigma Aldrich, St. Louis, Mo.). The cells were selected with 2 μg/ml puromycin (Sigma Aldrich, St. Louis, Mo.) and kockdown was verified by Western blot analysis.

Western Blot Analysis and Immunoprecipitation. Cells were treated with actinomycin D and TNFα, hydrogen peroxide ($H_2O_2$), hypoxia 1% for 24 hours or pre-treated with N-acetylcysteine (NAC), cobalt chloride ($CoCl_2$), YC-1 (Alexis Biochemicals, San Diego, Calif.), Resveratrol or nicotinamide (NAM) as described in the figure legends. All other chemicals were purchased from Sigma Aldrich (Sigma Aldrich, St. Louis, Mo.). Total proteins (30 μg) were lysed with RIPA lysis buffer and separated by sodium dodecylsulfate-polyacrylamide gel electrophoresis. After transfer, the polyvinylidene diflouride membrane was blocked with 5% non-fat milk in Tris-buffered saline with 0.1% Tween-20 (TBST) and then incubated with primary antibodies at 4° C. overnight. After washing, the horseradish peroxidase-conjugated secondary antibodies were added for 30 minutes at room temperature. Antibody binding was visualized by enhanced chemiluminescence reagent (GE Healthcare BioSciences, Buckinghamshire, United Kingdom).

For immunoprecipitation assays, cells were lysed in 1 ml of Nonidet P-40 (NP-40) extraction buffer. Cell lysate proteins (1 mg) were incubated with 1 μg anti-β-catenin antibody at 4° C. overnight rotation followed by A/G sepharose beads (Invitrogen, Camarillo, Calif.) for 4 hours. The immunoprecipitates were collected by centrifugation, washed 5 times with lysis buffer, and recentrifuged. Pellets were then resuspended in 2% sodium dodecylsulfate buffer, vortexed, and boiled at 100° C. for 5 minutes. Supernatants were collected and subjected to immunoblot analysis.

Antibodies used were: anti-β-catenin (Santa Cruz Biotechnology, Santa Cruz, Calif.), anti-HIF-1α (Novus Biologicals, Littleton, Colo.; BD Biosciences, San Jose, Calif.), anti-TCF4 (Sigma Aldrich, St. Louis, Mo.), K18D237 (Ana Spec, Fremont, Calif.)(66), anti-Flag M2 (Sigma Aldrich, St. Louis, Mo.), anti-acetylated-lysin (Cell Signaling Technology, Beverly, Mass.), anti-p21 (Santa Cruz Biotechnology, Santa Cruz, Calif.), anti-Sirt1 (Santa Cruz Biotechnology, Santa Cruz, Calif.). Anti-β-actin (Abcam, Cambridge, Mass.) served as a loading control.

Cell Proliferation and Survival.

For the assessment of cell proliferation and survival, a commercially available MTT (3-(4,5-dimethylthiazol-2-yl)-2,5-diphenyltetrazolium bromide) cell proliferation assay (Roche Applied Science, Indianapolis, Ind.) was used according to the manufacturer instructions. Absorbance was measured at 570 nm using a spectrophotometer.

Luciferase Reporter Assays.

For the reporter assay, cells were seeded in a 24-well plate under triplicate conditions at 80% confluency. Cells were transfected the next day with plasmid pMegaTOPFLASH and pMegaFOPFLASH (β-catenin reporter construct containing LEF1/TCF binding sites) or 5×-HRE (hypoxia response element) and 1 μg of pEF1/Myc-His/LacZ plasmid using Lipofectamine 2000 (Invitrogen, Carlsbad, Calif.). Six hours after transfection, the media was replaced with DMEM/F12 media. 24 hours after transfection, cells were either pretreated with drugs for one hour or incubated in hypoxia 1% for 24 hours as mentioned in the figure legends. After 2 days, luciferase and galactosidase expression were measured using the Dual-Light Reporter Gene Assay (Applied Biosystems, Foster City, Calif.) according to the manufacturer's instructions. Luciferase activity was normalized to β-galactosidase activity as an internal transfection control.

Detection of Apoptosis

Apoptosis was measured by western blot using Asp237 antibody that recognizes caspase-cleaved keratin18 or by using Caspase-Glo 3/7 Assay following the manusfacturer's instructions (Promega Corporation, Madison, Wis.). For caspase-Glo assay, in brief, cells were plated in white-walled 96-well tissue culture plates at a density of $5 \times 10^3$ cells per well in 100 μl of medium and allowed to adhere overnight. Cells were treated in triplicates for 24 hours with normoxia or hypoxia 1%. Caspase-Glo 3/7 reagent was added to each well in a 1:1 ratio and incubated for one hour before measuring luminescence using a LB96B dual injector luminometer (Berthold Technologies, Oak Ridge, Tenn.).

Determination of Intracellular ROS Levels.

The fluorescent probe, dichlorofluorescein diacetate (DCF-DA) (Invitrogen, Carlsbad, Calif.), was used to monitor the intracellular generation of ROS induced by hypoxia. After cells were incubated with 10 μmol/l DCF-DA for 30 min as previously described (67), cells were trypsinized, pelleted by centrifugation and resuspended in phosphate-buffered saline for FACS analysis by using a FACS LSRII flow cytometer (Becton Dickinson, San Diego, Calif.). The oxidized form of DCF-DA was excited at 488 nm and detected at 530 nm. Data were analyzed using CellQuest software.

In Situ ROS Detection by Dihydroethidium Labeling of Liver Tissue.

In situ reactive oxygen species (ROS) production was evaluated by staining with dihydroethidium (DHE) (Invitrogen), which is freely permeable across cell membranes. In the presence of ROS, dihydroethidium is oxidized to ethidium bromide and stains nuclei bright red by intercalating with the DNA. Fresh sections (8 μm) of unfixed, frozen liver tissues were immediately incubated with 3 μM dihydroethidium (diluted in phosphate-buffered saline from 5 mM stock solution in Me2SO) at 37° C. for 30 min in a humidified chamber. The slides were cover-slipped and fluorescence was detected with a fluoresecent microscope (Leica).

Quantitative Reverse-Transcription Polymerase Chain Reaction. RNA isolation was performed with the RNeasy Mini Kit (Qiagen Sciences, Valencia, Calif.). After DNase treatment, reverse transcription of 1.5 μg RNA was performed with Taqman Reverse Transcription Reagents (Applied Biosystems, Foster City, Calif.). Quantitative real-time PCR (qRT-PCR) was carried out using the Applied Biosystems Prism 7900HT Sequence Detection System and Sybr Green or Taqman PCR Master Mix (Applied Biosystems, Foster City, Calif.). Each measurement was performed in triplicate and the results were normalized to the expression of the glyceraldehyde-3-phosphate dehydrogenase (GAPDH) or β2-microglobulin (B2M) reference housekeeping gene. The primer sequences used are shown in table 1.

Statistical Analysis. All experiments were performed three times and representative data are presented. All data are expressed as the mean±standard deviation (SD). Data were evaluated by Student's t test to identify significant differences. Statistical significance was determined by a p value less than 0.05. A single asterisk (*) indicates p<0.05, two asterisks (**) indicate p<0.001, "NS" indicates not significant.

TABLE 1

Primer sequences
The following mouse primer sequences were used:

| Gene name | Primer sequences | |
|---|---|---|
| β-catenin | 5'-GTCAGCTCGTGTCCTGTGAA-3' | (SEQ ID NO: 1) |
| | 5'-GATCTGCATGCCCTCATCTA-3' | (SEQ ID NO: 2) |
| Cyclin D1 | 5'-TGGAGCCCCTGAAGAAGAG-3' | (SEQ ID NO: 3) |
| | 5'-AAGTGCGTTGTGCGGTAGC-3' | (SEQ ID NO: 4) |
| c-Myc | 5'-CTGTTTGAAGGCTGGATTT-3' | (SEQ ID NO: 5) |
| | 5'-TCGAGGTCATAGTTCCTGTT-3' | (SEQ ID NO: 6) |
| Axin2 | 5'-ACACATGCAGAAATGGGTCA-3' | (SEQ ID NO: 7) |
| | 5'-ACGTACGGTGTAGCCTTTGG-3' | (SEQ ID NO: 8) |
| GST | 5'-CTGTGGCTCCTGGTTCTCTC-3' | (SEQ ID NO: 9) |
| | 5'-TTGACTGGGAAGAGGGTGAG-3' | (SEQ ID NO: 10) |
| SOD1 | 5'-GACCTGGGCAATGTGACTGCTG-3' | (SEQ ID NO: 11) |
| | 5'-CACCAGTGTACGGCCAATGATG-3' | (SEQ ID NO: 12) |
| GPX1 | 5'-GACTGGTGGTGCTCGGTTTC-3' | (SEQ ID NO: 13) |
| | 5'-GTCGGACGTACTTGAGGGAATT-3' | (SEQ ID NO: 14) |
| iNOS | 5'-GGCAGCCTGTGAGACCTTTG-3' | (SEQ ID NO: 15) |
| | 5'-CATTGGAAGTGAAGCGTTTCG-3' | (SEQ ID NO: 16) |
| Cox2 | 5'-GTGGAAAAACCTCGTCCAGA-3' | (SEQ ID NO: 17) |
| | 5'-GCTCGGCTTCCAGTATTGAG-3' | (SEQ ID NO: 18) |
| GAPDH | 5'-GACGGCCGCATCTTCTTGT-3' | (SEQ ID NO: 19) |
| | 5'-CACACCGACCTTCACCATTTT-3' | (SEQ ID NO: 20) |

The following probes were purchased from Applied Biosystems:

| Gene name | Probe |
|---|---|
| HIF1α | Mm01283760_m1 |
| Epo | Mm01202755_m1 |
| VEGF | Mm01281449_m1 |
| Glut1 | Mm00600697_m1 |
| B2M | Mm00437762_m1 |

ABBREVIATIONS

ALT alanine aminotranferase
AST aspartate aminotransferase
BLI Bioluminescence Imaging
Cox2 cyclooxygenase 2
DCF-DA dichlorofluorescein diacetate
DHE dihydroethidium
Epo erythropoetin
FACS fluorescence activated cell sorting
Glut1 glucose transporter 1
GPX1 glutathione peroxidase 1
GST glutathione S-transferase
HRE hypoxia response element
iNOS inducible nitric-oxide synthase
IRI ischemia-reperfusion injury
LAP liver enriched activator protein (a.k.a. CEBP/β)
NAC N-acetylcysteine
RIPA buffer radioimmunoprecipitation assay buffer
SOD1 superoxide dismutase 1
TCF T cell factor
tetO-Cre tetracycline response element driving Cre
tTa tetracycline transactivating

---

What is claimed is:

1. A method of preventing or reducing liver tissue damage from ischemia or hypoxia in one or more organs or tissues oxidative stress due to an ischemic or hypoxic episode, comprising delivering to the individual an effective amount of a Wnt1 agonist in a pharmaceutically acceptable carrier.

2. The method of claim 1, wherein said Wnt1 agonist is human Wnt1 protein.

3. The method of claim 2, wherein the Wnt protein is formulated in a liposome.

4. The method of claim 2, wherein the human Wnt1 protein is delivered directly to the liver.

5. The method of claim 2, wherein the human Wnt1 protein is delivered to the individual prior to or during extraction of the organ liver tissue.

6. The method of claim 2, wherein the human Wnt1 protein is delivered to a recipient of the liver tissue prior to, during or after transplantation of the liver tissue into the recipient.

7. The method of claim 1, wherein the Wnt1 agonist is administered prior to an ischemic or hypoxic episode, concurrent with an ischemic or hypoxic episode, or both.

8. The method according to claim 1, wherein the tissue is selected from the group consisting of:
- an organ for transplantation; and
- an organ that is about to receive surgical treatment in which vascular occlusion followed by vascular reperfusion may occur.

9. A method of reducing oxidative stress-induced apoptosis of hepatocytes, the method comprising:
- contacting hepatocytes with a dose of Wnt1 polypeptide in a pharmaceutically acceptable carrier, wherein the dose is effective to reduce oxidative stress-induced apoptosis of said hepatocytes.

10. The method of claim 9, further comprising measuring apoptosis of said hepatocytes following said contacting with a dose of Wnt1 polypeptide.

11. The method of claim 9, wherein the Wnt1 polypeptide is formulated in a liposome.

12. The method of claim 9, wherein the Wnt1 polypeptide is administered prior to an ischemic or hypoxic episode.

* * * * *

SEQUENCE LISTING

<160> NUMBER OF SEQ ID NOS: 20

<210> SEQ ID NO 1
<211> LENGTH: 20
<212> TYPE: DNA
<213> ORGANISM: mouse

<400> SEQUENCE: 1
gtcagctcgt gtcctgtgaa                                           20

<210> SEQ ID NO 2
<211> LENGTH: 20
<212> TYPE: DNA
<213> ORGANISM: mouse

<400> SEQUENCE: 2
gatctgcatg ccctcatcta                                           20

<210> SEQ ID NO 3
<211> LENGTH: 19
<212> TYPE: DNA
<213> ORGANISM: mouse

<400> SEQUENCE: 3
tggagcccct gaagaagag                                            19

<210> SEQ ID NO 4
<211> LENGTH: 19
<212> TYPE: DNA
<213> ORGANISM: mouse

<400> SEQUENCE: 4
aagtgcgttg tgcggtagc                                            19

<210> SEQ ID NO 5
<211> LENGTH: 19
<212> TYPE: DNA
<213> ORGANISM: mouse

<400> SEQUENCE: 5
ctgtttgaag gctggattt                                            19

<210> SEQ ID NO 6
<211> LENGTH: 20
<212> TYPE: DNA
<213> ORGANISM: mouse

<400> SEQUENCE: 6
tcgaggtcat agttcctgtt                                       20

<210> SEQ ID NO 7
<211> LENGTH: 20
<212> TYPE: DNA
<213> ORGANISM: mouse

<400> SEQUENCE: 7
acacatgcag aaatgggtca                                       20

<210> SEQ ID NO 8
<211> LENGTH: 20
<212> TYPE: DNA
<213> ORGANISM: mouse

<400> SEQUENCE: 8
acgtacggtg tagcctttgg                                       20

<210> SEQ ID NO 9
<211> LENGTH: 20
<212> TYPE: DNA
<213> ORGANISM: mouse

<400> SEQUENCE: 9
ctgtggctcc tggttctctc                                       20

<210> SEQ ID NO 10
<211> LENGTH: 20
<212> TYPE: DNA
<213> ORGANISM: mouse

<400> SEQUENCE: 10
ttgactggga agagggtgag                                       20

<210> SEQ ID NO 11
<211> LENGTH: 22
<212> TYPE: DNA
<213> ORGANISM: mouse

<400> SEQUENCE: 11
gacctgggca atgtgactgc tg                                    22

<210> SEQ ID NO 12
<211> LENGTH: 22
<212> TYPE: DNA
<213> ORGANISM: mouse

<400> SEQUENCE: 12
caccagtgta cggccaatga tg                                    22

<210> SEQ ID NO 13
<211> LENGTH: 20
<212> TYPE: DNA
<213> ORGANISM: mouse

<400> SEQUENCE: 13
gactggtggt gctcggtttc                                       20

<210> SEQ ID NO 14
<211> LENGTH: 22
<212> TYPE: DNA
<213> ORGANISM: mouse

```
<400> SEQUENCE: 14
gtcggacgta cttgagggaa tt                                              22

<210> SEQ ID NO 15
<211> LENGTH: 20
<212> TYPE: DNA
<213> ORGANISM: mouse

<400> SEQUENCE: 15
ggcagcctgt gagacctttg                                                 20

<210> SEQ ID NO 16
<211> LENGTH: 21
<212> TYPE: DNA
<213> ORGANISM: mouse

<400> SEQUENCE: 16
cattggaagt gaagcgtttc g                                               21

<210> SEQ ID NO 17
<211> LENGTH: 20
<212> TYPE: DNA
<213> ORGANISM: mouse

<400> SEQUENCE: 17
gtggaaaaac ctcgtccaga                                                 20

<210> SEQ ID NO 18
<211> LENGTH: 20
<212> TYPE: DNA
<213> ORGANISM: mouse

<400> SEQUENCE: 18
gctcggcttc cagtattgag                                                 20

<210> SEQ ID NO 19
<211> LENGTH: 19
<212> TYPE: DNA
<213> ORGANISM: mouse

<400> SEQUENCE: 19
gacggccgca tcttcttgt                                                  19

<210> SEQ ID NO 20
<211> LENGTH: 21
<212> TYPE: DNA
<213> ORGANISM: mouse

<400> SEQUENCE: 20
cacaccgacc ttcaccattt t                                               21
```